United States Patent [19]

Janssens et al.

[11] Patent Number: 5,611,903

[45] Date of Patent: Mar. 18, 1997

[54] CAPILLARY ELECTROPHORESIS METHOD USING INITIALIZED CAPILLARY AND POLYANION-CONTAINING BUFFER AND CHEMICAL KIT THEREFOR

[75] Inventors: Jacques Janssens, Watermael-Boitsfort; Roland Chevigne, Wepion; Philippe Louis, Dalhem, all of Belgium

[73] Assignee: Analis S. A., Namur, Belgium

[21] Appl. No.: 412,032

[22] Filed: Mar. 22, 1995

[51] Int. Cl.$^6$ .................................................. G01N 27/26
[52] U.S. Cl. ........................................... 204/454; 204/601
[58] Field of Search ........................... 204/182.8, 299 R, 204/180.1, 450, 451, 454, 601

[56] References Cited

U.S. PATENT DOCUMENTS 4,997,536  3/1991  Ohms et al. ......................... 204/180.1
5,259,939  11/1993  Chen ................................. 204/180.1

OTHER PUBLICATIONS

Yao et al. (J. Chromatogr., A (1994), 663(1), 97–104, "Capillary Zone Electrophoresis of BAsic Proteins with Chitosan as a Capillary Modifier") 1994.

Tanaka, Y., et al., *Separation of enantiomers by affinity electrokinetic chromatography using avidin*, Electrophoresis (1994) 15:848–853 no month available.

Barker, G. E., et al., *Chiral separation of leucovorin with bovine serum albumin using affinity capillary electrophoresis*, Anal. Chem. (1992) no month available 64:3024–3028.

Valtcheva, L., et al., *Chiral separation of β–blockers by high–performance capillary electrophoresis based on non–immobilized cellulase as enantioselective protein*, Journal of Chromatography (1993) 638:263–267 no month available.

Damm, J. B. L., et al., *Separation of natural and synthetic heparin fragments by high–performance capillary electrophoresis*, Journal of Chromatography (1992) 608:297–309 no month available.

Honda, S., et al., *High–performance capillary electrophoresis of unsaturated oligosaccharides derived from glycosaminoglycans by digestion with chondroitinase ABC as 1–phenyl–3–methyl–5–pyrazolone derivatives*, Journal of Chromatography (1992) 608:289–295 no month available.

Kohr, J., et al., *Capillary electrophoresis with surface coated capillaries*, J. Microcol. (1991) 3:491–495 no month available.

Sirén, H., et al., *Introduction of migration indices for identification: Chiral separation of some β–blockers by using cyclodextrins in micellar electrokinetic capillary chromatography*, Electrophoresis (1994) 15:779–784 no month available.

(List continued on next page.)

*Primary Examiner*—Kathryn Gorgos
*Assistant Examiner*—Alex Noguerola
*Attorney, Agent, or Firm*—Knobbe, Martens, Olson & Bear

[57] ABSTRACT

A capillary electrophoresis detection and/or analysis method comprising the following steps:
  rinsing a ready-to-use capillary with an initiator to create an initialized capillary,
  adding a capillary buffer into the initialized capillary,
  injecting a sample to be analyzed (possibly diluted with a sample diluent) into the initialized capillary,
  optionally, adding a cathodic buffer to the cathodic end of the capillary, and
  submitting the sample to capillary electrophoresis.

In this method, the capillary and/or cathodic buffer comprise(s) a polyanion or a mixture of polyanions. The polyanion or the mixture of polyanions is included at least in the capillary or the cathodic buffer. The method can additionally comprise rinsing the capillary with NaOH after electrophoresis.

The present invention also includes a capillary electrophoresis detection and/or analysis unit, including an initiator and a capillary buffer and/or a cathodic buffer. The capillary and/or the cathodic buffer contain a polyanion or a mixture of polyanions.

25 Claims, 2 Drawing Sheets

OTHER PUBLICATIONS

Dette, C., et al., *Neutral and anionic cyclodextrins in capillary zone electrophoresis: Enantiomeric separation of ephedrine and related compounds*, Electrophoresis (1994) 15:799–803 no month available.

Busch, S., et al., *Chiral separations by complexation with proteins in capillary zone electrophoresis*, Journal of Chromatography (1993) 635:119–126 no month available.

Vespalec R., et al., *Prospects of dissolved albumin as chiral selector in capillary zone electrophoresis*, Journal of Chromatography (1993) 638:255–261 no month available.

Ishihama, Y., et al., *Optical resolution by electrokinetic chromatography using ovomucoid as a pseudo-stationary phase*, Journal of Chromatography A (1994) 666:193–201 no month available.

Nishi, H., et al., *Enantiomeric separation of drugs by affinity electrokinetic chromatography using dextran sulfate*, Electrophoresis (1994) 15:1335–1340 no month available.

Terabe, S., et al., *Effect of polymer ion concentrations on migration velocities in ion–exchange electrokinetic chromatography*, Journal of Chromatography (1990) 515:667–676 no month available.

Yao, X. W., et al., *Manipulation of electroosmotic flow in capillary electrophoresis*, Journal of Chromatography (1993) 636:21–29 no month available.

Karger, B., et al., *Capillary electrophoresis: Introduction and assessment*, Capillary Electrophoresis Technology (1993) 1:3–64 no month available.

Regnier, F. E., et al., *Chemical derivatization of fused silica capillaries*, Capillary Electrophoresis Technology (1993) 8:287–381 no month available.

Tsai, P., et al., *Direct control of electroosmotic flow in capillary electrophoresis by using an external electric field*, Capillary Electrophoresis Technology (1993) 13:475–488 no month available.

CAPILLARY ELECTROPHORESIS METHOD USING INITIALIZED CAPILLARY AND POLYANION-CONTAINING BUFFER AND CHEMICAL KIT THEREFOR

Field of the Invention

The present invention relates to an improved capillary electrophoresis detection and/or analysis method and to a unit for performing such a method.

BACKGROUND OF THE INVENTION

Perhaps the most rapidly developing area in separation science today is the burgeoning field of capillary electrophoresis (CE). The many unique features of this technology permeate all areas of chemistry, biology and medicine. Among the many unique features of capillary electrophoresis are its high power of resolution, high mass sensitivity, low sample volume requirements and overall sensitivity (Norberto A. Guzman Editor in Preface of Capillary Electrophoresis Technology. Marcel Dekker Inc. ISBN 0-8247-9042-1).

High-performance capillary electrophoresis (HPCE) has achieved remarkably rapid development since its introduction in the middle 1980s. Today more than 10 companies offer automated instrumentation and sales are expected to grow to approximately 150 millions dollars in 1996.

CE can be used for the separation of biomolecules such as proteins, peptides and DNA. For example, polyanions such as heparin (Separation of natural and synthetic heparin fragments by HPCE. Damm et al., Journal of Chromatography 1992; 608: 297–309) and oligosaccharides derived from glycosaminoglycans (Honda et al., Journal of Chromatography 1992; 608:28) have been analyzed with CE. However, there are still many serious problems to solve, such as loss of efficiency, poor reproducibility of migration time and electroosmotic mobility because of sample-wall interactions (J. Kohr and H. Engelhaardt pp.357 in Guzman).

Indeed these biomolecules are polyelectrolytes, meaning that they contain both negative and positive charges, the net charge being positive (when there is an excess of positive charges) at a pH below their pI, neutral at a pH equal to their pI, or negative (where there is an excess of negative charges) at a pH above their pI. When analyzing a mixture of polyelectrolytes such as serum proteins at a mid-range pH, some proteins are positively charged and tend to stick to the wall of the capillary, causing bad reproducibility. To minimize this phenomenon when separating such a mixture, one works usually at an extreme pH. The pH can be, for example, below 2.5 so that all proteins are positively charged, with as a consequence the saturation of the capillary wall. This results in weak electroosmotic flow (EOF) but high mobility for the proteins. Alternatively, pH can be above 10 so that all proteins are negatively charged and are driven mainly by the high electroosmotic flow.

But electroosmosis has several disadvantages (Regnier and Wu Chap.8 in Guzman). First, it shortens capillaries by eluting analytes from the column before electrophoretic resolution is complete. This problem can be reduced by the use of longer capillaries but at the expense of the analysis time. A second disadvantage of EOF is that, when coupled with the adsorption of cationic proteins, it can cause band-spreading and poor reproducibility of migration time. In some situations adsorbed protein can even reverse the surface charge at the head of the column. The net effect is that the rate, and even the direction, of electroosmotic pumping at the capillary wall can vary along the length of the column. Subsequently, complex flow profiles develop within the column that compromise efficiency. In addition, axial differences in either ionic strength or pH which alter zeta potential can diminish efficiency and influence analyte transport velocity.

Electroosmosis is an electrically induced flow caused by the presence of an ion gradient at the silica/water interface which results in a slight excess of positive ions migrating towards the cathode. This then results in a net flow towards the cathode resulting flow rate gives an additional velocity component to the ions migrating in the electric field, such that the total velocity ($v_{tot}$) of each molecule is the vector sum of the electrophoretic velocity (v) and the velocity imported by the electroosmotic flow $v_{eo}$. $V_{tot}$ can be expressed as follows:

$$\overline{v_{tot}} = \overline{v} + \overline{v_{eo}} \text{ with } \overline{v_{eo}} = \frac{L_d}{t_{eo}}$$

($t_{eo}$: observed migration time of electroosmotic marker);

$$\overline{v_{tot}} = \frac{L_d}{t_{tot}}$$

($t_{tot}$: observed migration time of molecule). Mobility μ is equal to:

$$\frac{v}{E} \text{ or } \frac{L_d/t}{v/L_t}$$

with
  E: electric field;
  $L_d$: capillary length from the anode to the detector;
  $L_t$: total capillary length; and
  t: time of the analyte.
Consequently:

$$\overline{\mu_{tot}} = \overline{\mu} + \overline{\mu_{eo}}$$

From this equation it can be seen that the electroosmotic flow adds the same velocity component to all analytes regardless of their ionic status. Consequently, a constant electroosmotic mobility (EOF) during analyses is necessary to obtain reliable analytical results from run to run, from day to day, from one capillary to another, or between different capillaries (when working with multiple capillaries).

The mobility $\overline{\mu}$ is related to the charge and the ionic status of the analyte by the formula:

$$\overline{\mu} = \frac{q}{6\pi\eta r}$$

with
  q: net charge;
  η: viscosity; and
  r: ionic radius.

From this equation it can be seen that neutral substances have a mobility $\overline{\mu}=0$ and then move with a mobility equal to $\overline{\mu}_{eo}$. Therefore, neutral substances move with the same $\overline{\mu}_{tot}=\overline{\mu}_{eo}$ whatever their radius or molecular weight and cannot be separated. From this equation it can also be seen that negative (or positive) substances of the same net charge and of the same radius but differing only by the position of a neutral functional group cannot be separated. In order to separate such neutral, negative, or positive substances, one must either make derivatives of such substances (pre-column derivatization or in-situ derivatization), these derivatives being charged, or one must use a buffer containing complexing or interacting species which can attract preferentially some functional group or polarizable group.

However, the velocity of the electroosmotic mobility is strongly dependent on many parameters, such as pH, ionic strength, the buffer composition and the chemical nature of the wall. The reproducibility of electroosmotic flow varies non-linearly with the pH, and the relative standard deviation (RSD) is usually higher between pH 4.5 and 7 than at lower or higher pH levels. (J. Kohr and H. Engelhardt J. Microcol. Sep. 1991;3:491)

The peak area in capillary electrophoresis is a function of the amount of sample present, its extinction coefficient, and the velocity of the solute peak. Unlike HPLC, the peaks in CE are travelling past the detector at different speeds. A slower-moving peak will have a greater-integrated area than a fast-moving peak, even if the extinction coefficient and amount of material are identical for each peak. Thus, a small change in the EOF may have dramatic effects on retention time (migration time) and peak area for both qualitative and quantitative applications (Tsai, Lee Direct control of EOF in CE by using an external electric field, p.476 in Guzman).

The total number of theoretical plates (N) is described by the equation $$N = \frac{(\bar{\mu} + \bar{\mu}_{eo})V}{2D}$$

where V is the voltage and D is the diffusion coefficient.

Therefore the highest efficiency is obtained when a molecule is migrating at the fastest velocity (i.e., at the largest value of $\mu_{tot}$). We can see that the electroosmotic flow helps speed up the separation in CE and thereby increases the separation efficiency. Further, the separation is directly proportional to the applied voltage (V) because a molecule that moves through the column quickly does not have much time to be spread out by longitudinal diffusion. Thus, working at high voltage and at the fastest velocity results in a very fast separation in the shortest analysis time. But such a short analysis time does not give the best separation. Indeed, the resolution (R) parameter that expresses the quality of the separation or the ability of the system to separate two closely eluting species is given by the following formula:

$$R = 0.117 \Delta \mu_{el} \left[ \frac{V}{D(\bar{\mu}_{eo} + \bar{\mu}_{el})} \right]$$

where:

V, D are the applied voltage and the diffusion coefficient;

$\Delta \mu_{el}$ is the difference in electrophoretic mobility between two species to be separated;

$\bar{\mu}_{eo}$ is the electroosmotic mobility; and $\bar{\mu}_{el}$ is the average electrophoretic mobility of the two species to be separated.

From this equation it can be seen that an increase can be obtained:

1) by increasing the voltage, though this increase is limited by the instrumentation capacity and by the increase of amperage, generating Joule heating and subsequent higher convection; and 2) by decreasing the diffusion coefficient by adding, for example, inert substances which result in longer migration times and also in higher Joule heating.

Once optimalized, all of these parameters are usually kept constant so that the only way to increase the resolution of closely migrating analytes is to decrease $\mu_{eo}$ in order to render the denominator of the third term in the formula above as low as possible. Higher resolution can be obtained when $\mu_{eo}=0$, but the gain in resolution achieved by decreasing or canceling $\mu_{eo}$ will be obtained at a large expense in analytical time (Tsai, Lee in Guzman page 475). Furthermore, negative substances moving with a velocity $v_{tot}= v_{eo}-v$ will migrate towards the anode once v becomes higher than $v_{eo}$ and then will not pass the detector.

Consequently, methods which use such a decrease or a cancellation of the electroosmotic mobility separate neutral and positive analytes. To resolve a mixture of neutral, negative and positive analytes, one must analyze such a mixture twice, either first with normal polarity and then with polarity reversal, or first at an acidic pH and then at a basic pH. Both methods generate two graphs, complicating or forbidding any quantification. Furthermore, when working in polarity reversal with $v_{eo}$ still positive, one cannot calculate the mobilities, since the neutral marker would not pass the detector. This leads to uncertainty in the identification of the peaks.

Various strategies have been devised to control or to suppress electroosmotic mobility using static coatings (permanent covalent chemical modification of the capillary surface by additives) or dynamic coatings by rinsing the capillary with additives before analysis or adding the additives in the buffer.

Kohr and Engelhardt (in Guzman, Chapter 10: CE with coated capillaries) conclude that capillary coating presents numerous problems such as reproducibility of coating procedures and the long-term stability of the capillary columns. No universal coating for the separation of proteins has yet been found. The following table is a compilation of their tables 1 and 2 with added data from the text:

| Functionality | pH range | Applications | Effect on EOF | Stability | Page |
|---|---|---|---|---|---|
| Trimethylsilyl | 7 | small molecules MECC | reduced | hydrolysis at higher pH | 363 |
| Amylpentafluor | 7 | proteins | retained | SD 7.6% day to day | 365 |
| Polyethylene glycol-Dial | 3–5 | proteins | reduced | no data at pH > 7 | |
| Polysaccharides protein | 8 | proteins | reduced or reversed | NA | 368 |
| Polyacrylamide | 2–8 | proteins | suppressed | not stable pH > 8 | 370 |
| Polyvinyl-pyrolidone | 2–6 | proteins | suppressed | | 373 |
| Polyethylen-cimine | 3–11 | proteins | reversed | | 375 |
| Poly (methyl-glutamate) | 1–9 | proteins | slightly reduced | | 375 |

Other additives used to decrease or to suppress the electroosmotic mobility, either dynamically or statically, are diamines and polyamines. These amines may be added to a buffer which does not contain any amine as the buffer itself and which is brought to the required pH by addition of a given acid. At a pH below their pI these amines are positively charged so that one positive end sticks to the negative wall of the capillary, exposing the other positive end(s) to the buffer. This suppresses the electroosmotic flow and can even reverse it.

Enantiomer separation is also an important field, not only in biochemistry but also in pharmaceutical analysis, where often one enantiomer is more active than the other and may be responsible for inadvertent side effects (e.g., Thalidomide-Softenon). Enantiomer separation by chiral capillary electrophoresis offers considerably greater efficiency with a shorter analysis time than GC or LC. Here again, screening of enantiomers by capillary electrophoresis requires more reliability than is presently available. Poor repeatability of the migration times due to the unsteady EOF is considered one of the most negative features of capillary electrophoresis. It is not likely that the development of coated capillaries and more standardized apparatuses will solve this problem (H. Siren, Jumppanen J, Manni Wen, Riekkola ML, Electrophoresis 1994; 15:779–84). These authors propose the use of two marker compounds to identify analytes on the basis of their mobility. However, chiral modifiers usually cause a decrease of the velocities and thus necessitate a longer analysis time.

In a recent paper (Dette C, Ebel S, Terabe S, Electrophoresis 1994; 15:799–803) a tetrakis (6-0-(4-sulfobutyl()-(-cyclodextrin sodium salt was used as a chiral selector. The authors note that these CDs, which are modified with negative groups, provide two features. They are still chiral selectors and have their own electrophoretic mobility opposite to the electroosmotic mobility. The latter could mean a better resolution when analytes with an opposite charge to the CD are used. The complex of the analyte with the negative CD derivative will have a negative mobility. For that reason a basic pH is necessary for good resolution.

Use of non-immobilized polyelectrolytes has also been described in capillary electrophoresis as a means to achieve chiral separation. For example, bovine serum albumin (Barker G, Russo P, Hartwick R, Anal Chem 1992; 64:3024–28), orosomucoid, ovomucoid, fungal cellulase and bovine serum albumin (Busch S, Kraak J, Poppe H, Journal of Chromatography 1993; 635:119–26) human albumin, bovine albumin (Vespalec R, Sustacek V, Bocek P, Journal of Chromatography 1993; 638:255–61), orosomucoid (Isaihama, Oda, Asakawa, Ijoshida, Sato, Journal of Chromatography 1994; A666:193–201) avidin in affinity electrokinetic chromatography (Tawaka, Matsubara, Terabe, Electrophoresis 1994; 15:848–53), and cellulase (Valcheva, Mohammad, Petterson, Hjerten, Journal of Chromatography 1993; 638:263–67) have all been proposed.

In a paper issued in October 1994 (Nishi, Nakamura, Nakai, Sato, Terabe, Enantiomer separation of drugs by affinity electrokinetic chromatography using dextran sulphate, Electrophoresis 1994; 15:1335–40), the authors used dextran sulphate (MW 7300) as a means to achieve chiral separations of some drugs at the expense of a decrease of the mobilities or an increase of the migration times not only of the solutes but also of the EOF marker as shown in their table 2.

| Concentration of dextran sulphate | 0.5 | 1 | 2 | 3 | 4 | 5 |
|---|---|---|---|---|---|---|
| Mobility of methanol | 3.617 | 3.438 | 3.392 | 3.375 | 3.351 | 3.142 |

Furthermore, their FIG. 7 demonstrates that decreasing the pH of the buffer from 6 to 5.5 increases the migration times of the solute by about 60%.

In Micellar Electrokinetic Chromatography (MEKC), a micelle incorporating a neutral substance is negatively charged and migrates towards the anode, but if the electroosmotic mobility is higher than the mobility of the micelle, the latter will be driven towards the cathode. In ion-exchange electrokinetic chromatography, the separation principle is based on the differential ion-pair formation of the analyte with a polymer ion having a charge opposite (positive) to that of the analyte (negative). Accordingly, an analyte ion bonded to the polymer ion through ion-pair formation migrates in the opposite direction of the free analyte ion. It is consequently possible that even analytes having identical electrophoretic mobilities will migrate with different velocities if their ion-pair formation constants are different (Terabe J, Isemura T, Journal of Chromatography 1990; 515:667–76). The polymers used are polycations polybrene and poly (diallyldimethylammonium chloride), and they result in an electroosmotic mobility towards the anode. For some separations, such as negative analytes at low pH, a polarity reversal is required, meaning that the sample is injected at the cathode instead of the anode, the detector being at the anode instead of the cathode.

To enhance separation resolution and to prevent protein adsorption, Tsai and Lee (Direct control of EOF in CE by using an external electric field, P. 476 in Guzman) propose a physical method involving the use of an additional perpendicular electric field applied from outside of the capillary for the direct control of the EOF. According to its polarity, this external electric field can increase or decrease the EOF.

This instrumental approach present the following advantages: only a type of capillary, a direct and dynamic manipulation of EOF, a high degree of optimization for the separation efficiency and resolution is achieved, and a higher degree of automation is established. But this is achieved at the expense of a higher instrument cost, two perfectly isolated "power supplies" being needed both working in the range of 10000 volts. Such power supplies cannot be used with most existing instruments. Furthermore, this technique does not eliminate protein adsorption (Yoo, Wu and Regnier, Manipulation of EOF in CE, Journal of Chromatography 1993; 636:21–29).

The last and probably the most important problem of CE is the capillary itself, or more precisely the preparation of the capillary prior to analysis. Indeed, capillaries cut from the same roll and prepared exactly in the same way may exhibit dramatic differences in EOF. For example, some may be rapidly equilibrated while others may require very long equilibration time, such as 24 hours of many runs, before being stabilized. Furthermore, a capillary which is stabilized for a given buffer may not be directly usable with another buffer and thus has to be stabilized again. If the first buffer is used thereafter, the capillary may need to undergo yet another stabilization procedure. Schomburg writes in Guzman page 315, in a chapter dealing with the chemistry of surface modification, that: "It is of great analytical interest if, in practice, fused silica capillaries can be easily produced that have defined EOF properties and adsorption of analyte molecules. Capillaries of reproducible performance should be obtainable by a simple procedure of etching and rinsing.

The process of equilibration before a capillary is conditioned for analytical separations should not require too much time. The aforementioned etching procedures are time-consuming and require long equilibration times before stable conditions for practical analyses are achieved. Therefore, it seems to be of interest to modify the silica surfaces by procedures, such as silanol derivation: ionic or non-ionic adsorption, as well as polymer coating. The time for equilibration between the buffer and the surfaces may be shortened, and the chemical properties of the coatings may be suited to suppress interaction or adsorption of special analyte molecules. The control of the electroosmotic flow and the suppression of analyte adsorption are the major aims of surface modifications."

ADVANTAGES OF THE PRESENT INVENTION

The present invention provides a new capillary electrophoresis detection and/or analysis method and unit which do not present the drawbacks of the state of the art and which are cheap, practical and easy to use. The present invention provides a method and unit which allow a direct stabilization of the EOF of a capillary after an initial etching with sodium hydroxide. Another advantage of the invention is that it provides a method and unit which allow the equilibration of capillaries to be standardized in such a way that different capillaries used in the same conditions generate the same EOF.

The present invention further provides a method and unit which allow a given capillary to get the expected EOF when changing the buffer or changing one or more constituents of a buffer to modify the pH, the ionic strength, or the molarity or adding additives to modify the resolution. Variations in the electroosmotic flow for a given buffer in function of the pH of the buffer are also minimized. In addition, about the same electroosmotic flow can be generated for different buffers of the same ionic strength at a given pH. Higher electroosmotic flow is possible, giving shorter analysis times (or higher velocities) and resulting in higher throughput and lower analysis costs. The invention provides better reproducibility of the migration times and better reproducibility of the quantitative determinations (the area of each peak) from run to run, from capillary to capillary, and between multiple capillaries.

The method and unit of the invention also allow the use of buffers with higher molarities or containing substances known to decrease the velocities of samples without sacrificing analysis time. Negative substances can be separated at acidic pH without changing the polarity and can be separated in a single run from either neutral substances or positive substances, or both together, according to the invention. The total number of theoretical plates can be increased, and the efficiency of the electrophoresis can be increased despite the decrease in the migration times.

The present invention further provides such a method and unit which enables an increase in the resolution between closely related species (e.g., chemicals, biochemicals, peptides, proteins) differing slightly by their charge, mass, substituent position, spatial configuration, etc. in reduced time. Species of the same charge but differing by functional groups or polarizable groups or differing by the position or the number of functional groups or polarizable groups can also be separated.

By using longer capillaries, higher resolution can be achieved in the same time as is achieved with a shorter capillary in the absence of the invention. Resolution of positive species of the same electrophoretic mobility but differing by their ion-pairing constants with a polyanion or a mixture of polyanions can also be achieved according to the invention while giving higher velocities, and thus shorter migration times, despite the decrease in the mobilities of the ion-paired species.

Yet another advantage of the invention is that it provides a highly versatile method and unit, meaning that the user can perform many separations without changing the capillary. The method is thus dynamic, as opposed to static coatings which are dedicated to a particular class of separations.

The above-mentioned advantages of the invention can also be achieved when an electrophoresis procedure is done with polarity reversal but also with a lengthening of the migration times and a decrease in the velocities.

SUMMARY OF THE INVENTION

The present invention concerns an improved capillary electrophoresis detection and/or analysis method comprising the following steps:

rinsing a ready-to-use capillary with an initiator (dynamic rinsing), adding a capillary buffer into the initialized capillary, injecting a sample (possibly diluted with a sample diluent if needed) to be analyzed into the capillary, adding, optionally, a cathodic buffer to the cathode end of the capillary, submitting the sample to capillary electrophoresis, wherein the capillary and/or cathodic buffer comprise(s) a polyanion or a mixture of polyanions with the proviso that the polyanion or the mixture of polyanions is included at least in the capillary or in the cathodic buffer, and rinsing with NaOH after electrophoresis.

Optionally, after the addition of the capillary buffer into the initialized capillary, the capillary may be rinsed with a buffer devoid of any polyanion, the injected sample being electrophoresed using buffer devoid of any polyanion.

The present invention concerns also a unit (i.e., a device) for the capillary electrophoresis detection and/or analysis of samples, comprising an initiator and (a capillary and/or a cathodic) buffer(s) comprising a polyanion or a mixture of polyanions, wherein the polyanion or the mixture of polyanions is included at least in the capillary and/or in the cathodic buffer.

Advantageously, the initiator is a polymer derivative having the following structure:

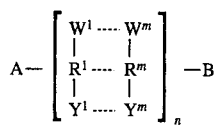

with m×n>12, wherein

A is H, OH, NH2, an alkyl, aryl, alkyl-aryl or heterocyclic skeleton and derivatives thereof, B is H, OH, NH2, an alkyl, aryl, alkyl-aryl or heterocyclic skeleton and derivatives thereof, $R^1$ to $R^m$ (i.e., $R^1 \ldots R^m$) are monomers (m being a whole number greater than 1), $R^1=R^2=\ldots=R^m$ or not, the resulting polymer being a homopolymer when $R^1=R^2=\ldots=R^m$ or the resulting polymer being a heteropolymer wherein at least one R is different from the other R groups, R representing an alkyl, aryl, alkyl-aryl, or heterocyclic skeleton or group (with one or more nitrogen atoms) and their derivatives, or a nucleotide or nucleic acid group, an amino acid or peptide group, or phosphate group, $W^1$ to $W^m$ (i.e., $W^1 \ldots W^m$) are H or a basic group chosen among the group consisting of imine, amine (primary, secondary, tertiary or quaternary amine), guanidine group or hydrazine group, and $Y^1$ to $Y^m$ (i.e., $Y^1 \ldots Y^m$) are H or any other group including an acidic radical, with the proviso that at the working pH, the initiator bears a net positive charge.

According to a preferred embodiment of the present invention, the initiator is a homopolymer R containing at least one nitrogen atom. According to another preferred embodiment of the invention, the initiator is a polypeptide or a protein. Advantageously, the polyanion is selected from the group consisting of a polysaccharide derivative, a synthetic polymer derivative, a polyacidic amino-acid, a polynucleotide, a polyphosphate or polyphosphonate, a polyphosphoric acid and/or a mixture thereof.

Preferably, the polyanion has the following structure:

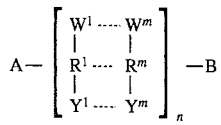

with m×n>12, wherein $R^1$ to $R^m$ are monomers, $R^1=R^2= \ldots =R^m$ or not, the resulting polymer being an homopolymer when $R^1=R^2= \ldots =R^m$ or the resulting polymer being a heteropolymer when one R is different from the other ones, R representing either P (phosphorus) or an alkyl, aryl, alkyl-aryl or a heterocyclic skeleton, A is H, OH, NH2, an alkyl, aryl, alkyl-aryl, a heterocyclic skeleton and derivatives thereof, B is H, OH, NH2, an alkyl, aryl, alkyl-aryl or a heterocyclic skeleton and derivatives thereof, $W^1$ to $W^m$ are H, OH, O, an acidic radical, or an alkyl, aryl, alkyl-aryl, or heterocyclic skeleton bearing an acidic radical, $Y^1$ to $Y^m$ are H, OH, an acidic radical or an alkyl, aryl, alkyl-aryl, heterocyclic skeleton bearing an acidic radical, an amine (primary, secondary or tertiary amine), a nitrogenous heterocycle or a mixture thereof, with the proviso that at the working pH the polyanion bears a net negative charge.

Preferably, the acidic radical of W to $W^m$ is chosen among the group consisting of carboxylic group, sulphate groups, sulphonate groups, guanidine groups, hydrazine groups or phosphate groups (mono-, di- or triphosphate groups).

According to a preferred embodiment, the polyanion has the formula $H_{n+2}P_nO_{3n+1}$ and has the following structure:

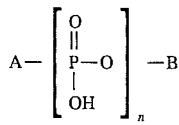

wherein n >12,

A is H, OH,

B is H, OH.

According to another preferred embodiment, the polyanion is a homopolynucleotide, a heteropolynucleotide, a ribonucleic acid or a deoxyribonucleic acid.

Preferably, the content of the polyanion and the initiator in the capillary comprises between $10^{-12}\%$ and 5% in relation to the whole liquid capillary volume. In one embodiment, the polyanion comprises about 1% by volume of the liquid in the capillary.

Advantageously, the pH of the buffer(s) is between 0.5 and 10.

DEFINITIONS

Figure 1:
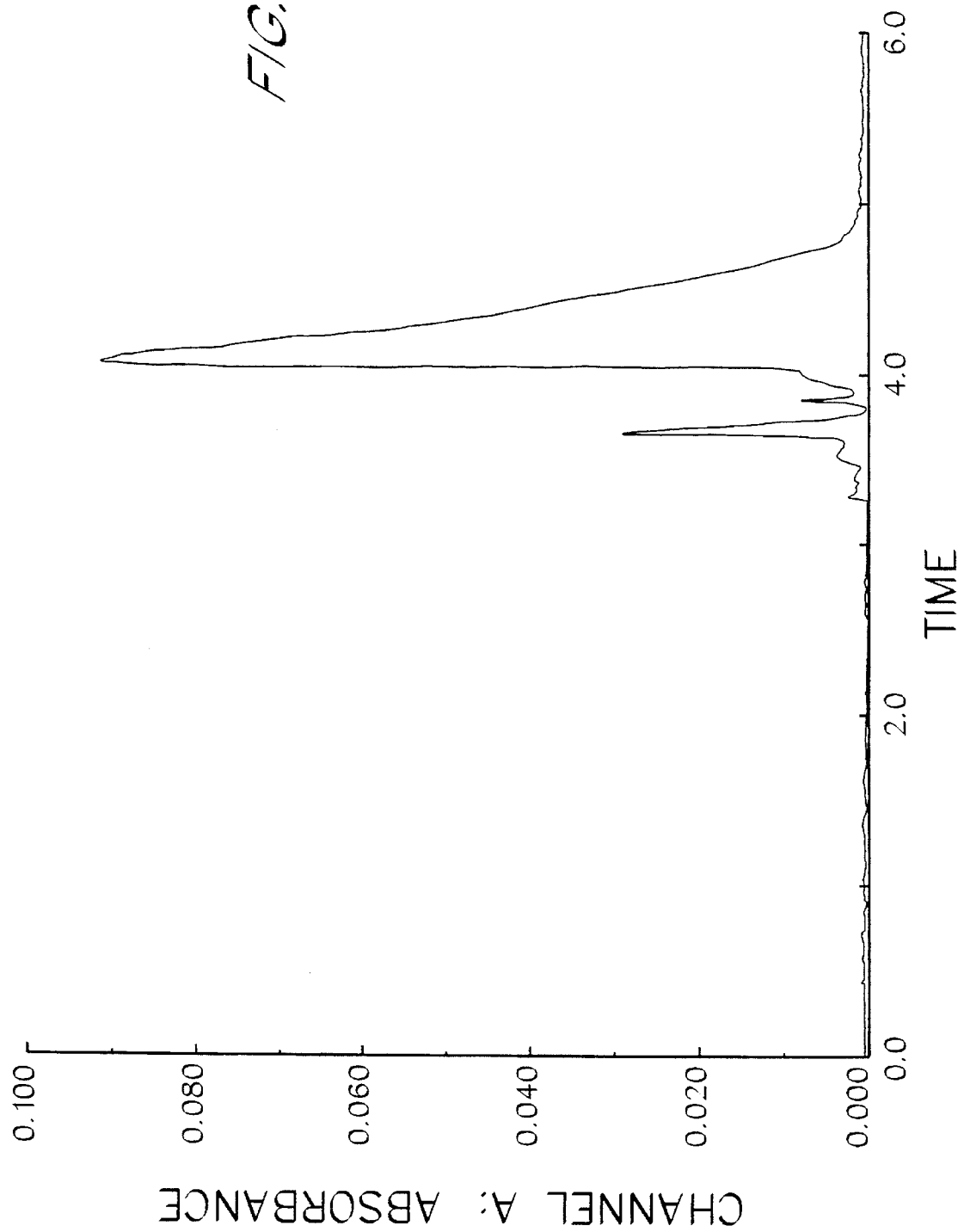
FIG. 1 displays the results of a scan showing the resolution between HbAla, HbAlb, HbAlc, Methemoglobin and HbA.

As used herein:

the term "capillary buffer" means the buffer present in the capillary prior to the injection of the sample;

the term "cathodic buffer" means the buffer at the cathode end of the capillary;

the term "anodic buffer" means the buffer at the anode end of the capillary;

the term "running buffer" means a buffer that is being used as the capillary buffer, the cathodic buffer and the anodic buffer;

the term "sample diluent" means any appropriate diluent for a sample, including running buffer at different concentrations or pH's, also including running buffer devoid of any polyanion;

the term "usual capillary electrophoresis method" means an electrophoresis method using no initiator and using buffer(s) devoid of any polyanion;

the term "initialized capillary electrophoresis method" means an electrophoresis method that involves the step of rinsing a capillary with an initiator followed by the step of rinsing the capillary with the capillary buffer or the running buffer; adding the sample; and performing a separation using running buffer or cathodic buffer and anodic buffer;

the term "initiator" means a rinsing solution of any molecule or mixture of molecules of high molecular weight (molecular weight higher than 1000 M.W., preferably higher than 5000 M.W.) bearing some positive charges at the pH of the diluent in which it is dissolved or at the pH of the buffer. The initiator works dynamically. It is a polycation when it bears only positive charges and is a polyelectrolyte when it bears positive and negative charges;

the term "ready-to-use capillary" means a stabilized or unstabilized capillary that has been subjected to a procedure such as the following: rinsing with NaOH 0.1 M/L for 15 min., then with $H_2O$ for 5 min., then with NaOH 0.1 M/L for 5 min., then with $H_2O$ for 5 min., then with an appropriate buffer for 10 min;

the term "stabilized capillary" means a capillary which has been stabilized during an equilibration time varying from 30 min. to several days before becoming stabilized, this equilibration depending upon the buffer and the pH of the buffer, and varying from capillary to capillary, even between capillaries of the same manufacturing lot number. Repetitive analyses using a stabilized capillary display EOF measurements showing a dispersion around the mean value;

the term "unstabilized capillary" means a capillary which has not been stabilized. Repetitive analyses using an "unstabilized capillary" display EOF measurements showing a continuous drift, either ascending or descending;

the term "electrophoretic velocity of a component $v_{tot}$" is to be calculated by dividing the length of the capillary from the injection (addition) point to the detector $L_D$ by the observed migration time of the component, as in the formula below:

$$v_{tot} = \frac{L_D}{t}$$

the term "electroosmotic velocity" or $v_{eo}$ is defined as:

$$v_{eo} = \frac{L_d}{t_{eo}}$$

where $t_{eo}$ is the observed migration time of a neutral marker such as dimethyl formamide (DMF);

the term net velocity of a component V is defined as:

$$v = v_{tot} - v_{eo} = L_D \left( \frac{1}{t} - \frac{1}{t_{eo}} \right) \text{ or } L_D \left( \frac{t_{eo} - t}{t_{eo} \cdot t} \right)$$

the term "$v_{ip}$" means the velocity of a positively charged component, the net charge of which has been decreased, canceled or rendered negative by interaction with a negatively charged polyanion; and the term "mobility of a component" $\mu$ is determined with the formula:

$$\mu = \frac{v}{E} = \frac{1}{E}(v_{tot} - v_{eo}) = \frac{L_D}{E} \left( \frac{1}{t} - \frac{1}{t_{eo}} \right) \text{ with } E = \frac{V}{L_t}$$

then $$\mu = \frac{L_D \cdot L_t}{V} \left( \frac{1}{t} - \frac{1}{t_{eo}} \right)$$

E being the electrical field, V the voltage and $L_t$ the total length of the capillary. For a given capillary and working at the same voltage and comparing experiments being done with the same capillary, the factor $$\frac{L_D \cdot L_t}{V}$$

is a constant, then $\mu$ is directly proportional to $$\frac{1}{t} - \frac{1}{t_{eo}} \text{ or } \frac{t_{eo} - t}{t_{eo} \cdot t}$$

DETAILED DESCRIPTION OF PREFERRED EMBODIMENTS OF THE INVENTION

The initialized capillary electrophoresis method of the present invention differs from usual capillary electrophoresis methods by the fact that prior to the usual step of rinsing the capillary with a running buffer, a short rinse with a solution of initiator is first performed, followed by a rinsing step with a running buffer containing a polyanion or a mixture of polyanions.

The initiator according to the invention, some typical representatives of which are listed in table 1, is a polyelectrolyte or a mixture of polyelectrolytes, preferably a macromolecule, bearing acidic or basic groups which can become negatively and positively charged. Such a polyelectrolyte can be a protein or a mixture of proteins.

The initiator according to the invention is a polycation or a mixture of polycations of high molecular weight, a monomer of which bears one or more basic group(s) which can become positively charged. Such a polycation can be a synthetic polymer bearing primary, secondary, tertiary or quaternary amines. Such a polycation can be a polyelectrolyte such as a polyaminoacid, aminoacids of which are basic aminoacids or are random copolymers of such basic aminoacids.

Table 1 shows the effect on EOF of a usual capillary electrophoresis method and the initialized electrophoresis method using different initiators and the same polyanion.

TABLE 1

| Exemplative list of initiators and their effects on EOF | | |
|---|---|---|
| | Mean time | RSD |
| Usual capillary electrophoresis method | 14.954 | 0.96 |
| Initialized capillary electrophoresis method | | |
| Initiator: | | |
| Aminoglucosydase 0.2% | 9.23 | 2.6 |
| Pepsine 0.2% | 10.65 | 1.5 |
| Orosomucoid 0.1% | 10.249 | 1.2 |
| Lysozyme | 15.2 | |
| Subtilisin | 11.712 | |
| Amylase | 9.84 | |
| Urease Jack beans 0.17% | 2.93 | 0.25 |
| Urokinase | | |
| LMW | 11.406 | |
| HMW | 11.512 | |
| Kininogen | | |
| LMW | 9.471 | |
| HMW | 7.084 | |
| Streptavidin | 11.192 | |
| Ficin | 8.826 | |
| Bromelin | 9.981 | |
| Protease 0.5% | 10.562 | |
| Poly Glu—Lys(6:4) MW 56000 | | |
| 0.017% | 4.464 | 0.37 |
| 0.033% | 4.765 | 0.24 |
| Poly Glu—Lys(6:4) MW 56000 | | |
| 0.066% | 4.521 | |
| 0.1% | 4.5 | |
| 0.33% | 4.06 | 0.15 |
| 0.66% | 4.118 | 0.33 |
| Poly Lys—Ala(1:1) 41600 0.1% | 2.609 | 2.71 |
| Poly Lys—Ala(2:1) 50000 0.1% | 2.564 | 0.94 |
| Poly Lys—Ala(3:1) 35000 0.1% | 2.516 | 0.21 |
| Poly Ornithine 145000 0.1% | 2.498 | 1.4 |
| Poly Histidine 22000 0.1% | 2.464 | 0.19 |
| Poly Arg—Ser(3:1) 22000 0.1% | 2.463 | 0.89 |
| Poly Arg—Pro—Thr(6:3:1) 18000 0.1% | 2.9924 | 14.1 |
| Poly Ala—Lys 153000 0.1% | 2.563 | 3.64 |
| Poly Arg 156000 0.1% | 2.235 | |
| Pre Albumin Human | 11.028 | |
| Albumin bovine | 2.96 | |
| Albumin bovine glycated | 4.7 | 2.8 |
| Albumin bovine cystinyl | 3.184 | 0.46 |
| Albumin bovine cellobiosyl | >10 | |

TABLE 1-continued

Exemplative list of initiators and their effects on EOF

| Usual capillary electrophoresis method | Mean time 14.954 | RSD 0.96 |
|---|---|---|
| Albumin bovine carboxymethyl | | |
| 0.17% | 3.119 | 0.47 |
| 0.25% | 3.022 | |
| 0.34% | 3.122 | 0.2 |
| 0.5% | 3.076 | 0.17 |
| 0.34(½) | 3.126 | 1.4 |
| Albumin bovine fucosylamide | | |
| 0.13% | 2.625 | |
| 0.2% | 2.617 | 0.37 |
| 0.27% | 2.605 | 0 |
| 0.4% | 2.594 | 0.25 |
| Albumin bovine Nacetyl βD 0.16% glucosaminidide | 2.553 | 0.3 |
| 0.08% | 2.656 | 1.3 |
| 0.22% | 2.718 | 0.17 |
| 0.1% | 2.663 | 0.5 |
| Albumin cat | 3.77 | 0 |
| Albumin chicken | >10 | |
| Albumin horse | 2.995 | 0 |
| Albumin human | 2.956 | 0.9 |
| Albumin rabbit | 3.373 | 0.075 |
| Albumin sheep | 3.149 | 0.16 |
| Albumin turkey | 3.672 | 0.11 |
| Hemoglobin human | 2.912 | 0.26 |
| Hemoglobin bovine | | |
| 0.17% | 2.93 | 0.4 |
| 0.34% | 2.8 | |
| 0.5% | 2.81 | 0.55 |
| Hemoglobin bovine NN (dimethylated) | | |
| 0.17% | 2.891 | 0.11 |
| 0.34% | 2.831 | 0.14 |
| 0.5% | 2.793 | |
| 0.75% | 2.777 | 0.075 |
| Human serum 0.4% | 3.549 | 0.31 |
| Human plasminogen 0.2% | 6.118 | |
| Human alpha 2 macroglobulin | 4.912 | |
| Lectin Triticum Vulgaris MW 36,000 | | |
| 0.16% | 8.85 | 0.58 |
| 0.32% | 7.6 | 4.6 |
| 0.64% | 7.153 | 4 |
| Lectin from Helix pomatia | 6.996 | |
| Solanum | 7.268 | |
| Bandaraea | 10.947 | |
| Lectin from | | |
| *Lens culinaris* | 3.79 | 2.9% |
| *Perseau americana* | 9.07 | |
| *Arachis hypogea* | 6.186 | |
| Boulinia | 9.532 | |
| Concanavalin 1 | | |
| type VI | 10.294 | |
| type V | 8.941 | |
| type III | 11.235 | |
| Succinyl concavanalin A | 10.038 | |
| Polyethyleneimine 60000 | | |
| 0.033% | 3.349 | 6 |
| 0.1% | 3.63 | 2.4 |
| 0.16% | 3.45 | 6.5 |
| Polyethyleneimine 600000 | | |
| 0.033% | 3.34 | 0.3 |
| 0.1% | 3.256 | 0.26 |
| 0.16% | 3.21 | 1.8 |
| Polybrene | | |
| 0.033% | 2.178 | 0.31 |
| 0.16% | 2.235 | 0.68 |
| Diethylaminoethyldextran 600,000 | | |
| 0.033% | 2.38 | 1.35 |
| 0.1% | 2.424 | 0.19 |
| Diethylaminoethyldextran 600,000 0.16% | 2.426 | 0.09 |
| Poly {1-[4-(3 carboxy-4 hydroxy-phenilazo)benzesulphonamido]-1, 2 ethenediyl} | 2.8 | — |
| Polyoxyethylene bis (3 amino-2 hydroxypropyl) | 9.441 | — |
| Polyoxyethylene bis (6 aminohexyl) | 2.61 | |
| Polyallylamine high MW | 2.412 | |

NA: less than 5 replicates; RSD not calculated.

Buffer usual capillary electrophoresis method:
  TRIS/malic acid 150 mM/L, pH 4.625.

initialized capillary electrophoresis method:
  as in the usual capillary electrophoresis method with 0.01% chondroitin sulphate.

initiator:
  various proteins, polypeptides, polycations or polymers at 0.25% concentration (when not indicated, some at different concentrations (indicated).

Instrument:
  PACE 2000, same cartridge, same stabilized capillary 25 μ×23 cm.

Separation performed at 12 KV.

Generally the more of an excess of basic groups there is, the more efficient the initiator will be.

The polyanions according to the invention, of which some typical representatives are listed in table 2, are characterized by the following properties: they are soluble polymers with repeating units (a monomer of which comprises at least one acidic group such as carboxylate, sulphate, sulphonate, phosphate, etc.) which give a net negative charge to the polymer.

Table 2 shows a comparison between a usual capillary electrophoresis method and the initialized capillary electrophoresis method using different polyanions.

TABLE 2

Exemplative list of some polyanions and their effects on EOF

| Usual capillary electrophoresis method | Mean time 14.954 | RSD 0.96 |
|---|---|---|
| Initialized capillary electrophoresis method | | |
| Polyanions: | | |
| Chondroitin sulphate | 3.146 | 0.89 |
| Heparin pig intestine | 3.511 | 0.11 |
| Heparin pig (MW 4000–6000) | 4.875 | 0.54 |
| Heparin bovine intestine | 3.391 | 0.22 |
| Sulodexide (Heparin-like) | 3.992 | 0.61 |
| Den sulphated heparin porcine intestine | 4.493 | 0.27 |

TABLE 2-continued

Exemplative list of some polyanions and their effects on EOF

| Usual capillary electrophoresis method | Mean time 14.954 | RSD 0.96 |
|---|---|---|
| Mesoglycan (Heparin-like) | 4.076 | 1.7 |
| Dextran sulphates having the following molecular weights (MW): | | |
| 5000 | 3.61 | 1.05 |
| 8000 | 3.761 | 0.3 |
| 15000 | 4.014 | 0.49 |
| 40000–100000 | 2.388 | 0.49 |
| 500000 | 2.262 | 0.22 |
| 1000000 | 2.254 | 0.29 |
| Alginic acid low viscosity | 2.625 | 0.29 |
| Alginic acid medium viscosity | 2.503 | 0.66 |
| Alginic acid high viscosity | 2.5 | 0.95 |
| Alginic acid unspecified from Sigma | 3.333 | 0.25 |
| Alginic acid unspecified from Fluka | 3.948 | 0.1 |
| Alginic acid unspecified from Janssen | 2.467 | 0.18 |
| Polygalacturonic acid from Fluka MW 25000–50000 | 3.354 | 0.06 |
| Polygalacturonic acid from Sigma | 3.485 | 0.17 |
| Hyaluronic acid | 3.59 | 1.6 |
| Carboxymethyl cellulose ultra low viscosity | 4.908 | 1.39 |
| Carboxymethyl cellulose MW 700000 | 2.601 | 0.26 |
| Polyaspartic acids: | | |
| 593 | 10.063 | 0.57 |
| 6800 | 6.207 | 0.71 |
| 22900 | 3.616 | 0.54 |
| Polyglutamic acid MW 34000 | 5.059 | |
| Poly Glu—Lys 6:4 MW 56000 | 14.745 | |
| Poly Glu—Ala 6:4 MW 30000 | 7.765 | |
| Polyinosinic acid | 4.067 | 1.9 |
| Polyadenylic acid | 2.836 | 0.2 |
| Polyadenilic-cytidylic acid | 4.276 | 0.48 |
| Polyguanylic acid | 2.843 | 0.53 |
| Polycytidylic-guanylic acid | 2.55 | 0.31 |
| Polyuridylic acid | 3 | |
| Polyadenylic-cytidylic-inosinic acid | 6.091 | |
| Polyadenylic-cytidylic-guanilic acid | 4.5 | |
| Polyadenylic-cytidylic-uridylic acid | 6.8 | |
| DNA | 5.544 | 0.86 |
| RNA Yeast | 10.784 | |
| Polyacrylic acids having the following molecular weights: | | |
| 1200 | 9.58 | 0.96 |
| 2100 | 9.361 | 0.84 |
| 5100 | 6.118 | 0.16 |
| 20000 | 4.031 | 0.12 |
| 60000 | 3.4 | 0.09 |
| 170000 | 3.199 | 0.34 |
| 450000 | 2.699 | 0.13 |
| Polyacrylamidomethylpropane sulfonic acid | 2.462 | 0.9 |
| Polystyrene sulfonic acid MW 70000 | 2.541 | 0.53 |
| Polyvinyl sulphonic acid | 4.441 | 0.38 |
| Polyanetholsulphonic acid | 2.993 | 2 |
| Poly(acrylic acid-co-maleic acid) having the following molecular weights: | | |
| 3000 | 4.887 | 0.37 |
| 50000 | 3.203 | 0.4 |
| 70000 | 3.227 | 0.33 |
| Polyl(1 vinylpyrolidone-Co acrylic acid) | 5.704 | 0.38 |
| Methylvinyl ether/maleic acid copolymer | 2.355 | 0.43 |
| Polyvinylamide - Co acrylic acid | 2.884 | 0.12 |
| Poly{1-[4-(3 carboxy-4 hydroxy-plenylazo)benzenesulphonamidol]} 1.2 ethediyl | 5.216 | |
| Sodium polyphosphate (P13–P18) | 6.88 | 0.3 |
| Polyphosphoric acid | 9.269 | 0.28 |

Buffer:

usual capillary electrophoresis method:
TRIS/malic acid 150 mM/L, pH 4.605.

initialized capillary electrophoresis method:
as in the usual capillary electrophoresis method with 0.01% of different polyanions.

initiator:
pig albumin 0.2% dissolved in the usual capillary electrophoresis method.

Instrument:
PACE 2000, same cartridge, same stabilized capillary 25 μ×23 cm for the usual capillary electrophoresis method.

No stabilization was done for the initialized capillary electrophoresis method. Voltage was 12 KV.

The determination of EOF (DMF) was made 5 times. The mean time in minutes (min.) and the RSD are tabulated.

Other polyanions have been tested successfully, although not in the above conditions, including chondroitin sulphate from various animals and from various tissues, heparin sulphate, dermatan sulphate, polysialic acid, colominic acid, polyaspartic acids and polyglutamic acids and derivatives of both, random copolymers of aspartic acids and glutamic acids, and polyacrylic acids of MW (molecular weight) up to 4000000.

In the presence of an electrical field the polyanions migrate towards the anode, i.e. against or in countercurrent to the electroosmotic flow (table 3), resulting not only in a stabilization of the electroosmotic flow but unexpectedly yielding an improvement of the reproducibility of the velocities of the EOF and also of the velocities of the species to be separated.

TABLE 3

Velocity of chondroitin sulphate towards the anode (Mean of 5 replicates)

| Chondroitin sulphate % | Capillary buffer | Cathodic buffer | Time Min. | RSD | Velocity cm/min. | Time EOF min. | RSD | Velocity EOF cm/sec. |
|---|---|---|---|---|---|---|---|---|
| 0.01% | UCEM | ICEM | 0.977 | 0 | −6.86 | 4.713 | 0.29 | +3.39 |
| 0.02% | UCEM | ICEM | 0.977 | 0 | −6.86 | 4.444 | 0 | +3.6 |

TABLE 3-continued

Velocity of chondroitin sulphate towards the anode (Mean of 5 replicates)

| Chondroitin sulphate % | Capillary buffer | Cathodic buffer | Time Min. | RSD | Velocity cm/min. | Time EOF min. | RSD | Velocity EOF cm/sec. |
|---|---|---|---|---|---|---|---|---|
| 0.04% | UCEM | ICEM | 0.977 | 0 | −6.86 | 4.31 | 0 | +3.71 |
| 0.08% | UCEM | ICEM | 0.977 | 0 | −6.86 | 4.195 | 0 | +3.81 |
| 0.01% | ICEM | UCEM | 1.478 | 0.57 | −4.53 | 3.42 | 0.32 | +4.68 |
| 0.02% | ICEM | UCEM | 1.478 | 0.74 | −4.53 | 3.304 | 0.27 | +4.84 |
| 0.04% | ICEM | UCEM | 1.562 | 0.55 | −4.29 | 3.234 | 0.21 | +4.95 |
| 0.08% | ICEM | UCEM | 1.568 | 0.33 | −4.27 | 3.25 | 0.27 | +4.96 |

Buffer:

usual capillary electrophoresis method (UCEM) Malic/TRIS 150 mM/L pH 4.629.

initialized capillary electrophoresis method (ICEM) same as in the usual capillary electrophoresis method but with four different percentages of chondroitin sulphate.

Initiator:

Pig albumin 0.2% in buffer without chondroitin sulphate.

Capillary:

25 μ×23.7 cm, detector at 6.7 cm from the cathode.

Velocity of chondroitin sulphate and DMF with polyanion present only in the cathodic buffer or only in the capillary buffer was determined.

When the chondroitin sulphate is only in the cathodic buffer, the time is determined by the increase of absorbance once the chondroitin sulphate passes the detector coming from the cathodic buffer (migration length 6.7 cm).

When the chondroitin sulphate is only in the capillary buffer the time is determined by the decrease of absorbance once the chondroitin sulphate is no more present before the detector (length of migration 6.7 cm).

Initially, the use of the initiator was intended as a means to saturate the sites of adsorption of the capillary wall to prevent adsorption of cationic species. Use of such initiator prior to a usual capillary electrophoresis method generated incoherent results: shortening of migration times with increased RSD, lengthening of migration times with decreased RSD. When strongly positively charged initiators are used, they induce, in the absence of polyanion, a reversal of the electroosmotic flow, which then goes to the anode, these initiators having rendered the charge of the capillary wall positive (table 4).

TABLE 4

Capillary charge reversal by initiators

| | Time EOF (min.) | | | | Velocity EOF (cm/min.) | | | |
|---|---|---|---|---|---|---|---|---|
| Initiator | TRIS/MALIC UCEM | Buffer ICEM | PHOSPHATE ICEM | Buffer ICEM | TRIS/MALIC UCEM | Buffer ICEM | PHOSPHATE UCEM | Buffer ICEM |
| Polyethylenimine MW 60000 | | | | | | | | |
| 0.033% | 1.418 | 3.349 | | | −11.99 | +5.08 | | |
| 0.1% | 1.467 | 3.63 | 2.612 | 1.69 | −11.59 | +4.68 | −6.5 | +10.06 |
| 0.16% | 1.522 | 3.45 | | | −11.17 | +4.92 | | |
| Polyethylenime MW 600000 | | | | | | | | |
| 0.033% | 1.796 | 3.34 | | | −9.47 | +5.09 | | |
| 0.1% | 1.906 | 3.256 | 2.643 | 1.649 | −8.92 | +5.22 | −6.43 | +10.31 |
| 0.16% | 2.047 | 3.21 | | | −8.3 | +5.29 | | |
| Polybrene | | | | | | | | |
| 0.033% | 2.038 | 2.178 | | | −8.34 | +7.81 | | |
| 0.1% | 1.882 | | 2.188 | 1.633 | −9.03 | | −7.77 | +10.47 |
| 0.16% | 1.773 | 2.235 | | | −9.58 | +7.6 | | |
| Diethylaminoethyl-dextran | | | | | | | | |
| 0.033% | 1.584 | 2.38 | | | −10.73 | +7.14 | | |
| 0.1% | 1.427 | 2.424 | 2.424 | 1.621 | −11.91 | +7.01 | −7 | +10.49 |
| 0.16% | 1.42 | 2.426 | | | −11.97 | +7 | | |
| PPO 0.033% | 1.882 | 2.8 | 3.522 | | −9.03 | +6.07 | −4.83 | |

Buffer:

usual capillary electrophoresis method TRIS/MALIC 150 mM/L pH 4.625, no polyanion. Phosphate/NaOH 100 mM/L pH 2.617.

initialized capillary electrophoresis method TRIS/MALIC 0.01% chondroitin sulphate. Phosphate 0.1% chondroitin sulphate.

Working in polarity reversal (12 KV), the electroosmotic flow goes to the anode and velocities are negative. However, while in the presence of a polyanion (working in normal polarity) the velocities are positive.

Originally, the use of the polyanions was intended as a means to perform ion-pairing with positively charged substances and it was discovered that some polyanions increased the electroosmotic flow in certain conditions of pH while they decreased the electroosmotic flow in other conditions of pH. Furthermore, the effects varied strongly with the nature of the buffer used. At the same pH one polyanion generated higher electroosmotic flow in a given buffer, while in another buffer at the same pH the polyanion decreased the electroosmotic flow.

But unexpectedly, the use of an initiator conjointly with a polyanion, as in the present initialized capillary electrophoresis method, resulted in an enhancement of the effects of the polyanions. The mechanism of action of the initiators in such an initialized capillary electrophoresis method is not fully understood. It is speculated, however, that one positive site (at least) of the initiator sticks to a negative site of the capillary wall, thus exposing an excess of positive charges to the lumen of the wall, as the net charge of the initiator is positive. This excess of positive charges allows a binding of the negatively charged polyanions to the capillary wall, and as these are polymers, a lot of negative charges are thus exposed to the lumen capillary. When strongly positively charged initiators are used, they induce, in the absence of polyanion, a reversal of the electroosmotic flow which then goes to the anode, these initiators having rendered the charge of the capillary wall positive (table 4).

Indeed, when the capillary is rinsed with the initiator and then with the capillary buffer followed by a rinsing with the same buffer devoid of polyanion, and the electrophoresis is performed using buffers devoid of polyanion, the enhancement effect on the electroosmosis remains. Further analyses using a usual capillary electrophoresis method demonstrate that the enhancement of the electroosmosis becomes less and less pronounced and disappears totally after 4–5 analyses, provided that after the first electrophoresis the capillary is rinsed with the buffer devoid of any polyanion instead of with sodium hydroxide. Once sodium hydroxide is used to rinse the capillary after electrophoresis, no remnant effect can be seen.

The initialized capillary electrophoresis method employing a ready-to-use stabilized capillary or unstabilized capillary generates the same EOF (table 5) for the same buffer, which means that changing a capillary or replacing a capillary within a battery of multiple capillary instruments avoids having to stabilize and equilibrate the new capillary, meaning that the user has to perform only the ready-to-use capillary step and then can proceed directly to further analyses. In the same way, when replacing one buffer with another, the initialized capillary electrophoresis method allows one to immediately get the expected EOF for the new buffer, avoiding again any equilibration step (table 6).

TABLE 5

Direct stabilization of EOF for different capillaries

| Capillary | Time in min. | | RSD | |
|---|---|---|---|---|
| | ICEM | UCEM | ICEM | UCEM |
| 1 | 2.383 | 4.2 | 0.26 | 3.13 |
| 2 | 2.397 | 3.926 | 0.27 | 3.68 |
| 3 | 2.443 | 4.322 | 0.35 | 3.73 |
| | | (4.99–5.13) | | (8.5–2.34) |
| 4 | 2.413 | 4.291 | 0.84 | 4.63 |
| 5 | 2.424 | 4.11 | 0.37 | 5.42 |

TABLE 5-continued

Direct stabilization of EOF for different capillaries

| Capillary | Time in min. | | RSD | |
|---|---|---|---|---|
| | ICEM | UCEM | ICEM | UCEM |
| 6 | 2.423 | 4.327 | 0.24 | 2.72 |
| 8 | 2.438 | 4.558 | 0.45 | 2.04 |
| 9 | 2.399 | 8.6 | 0.38 | 10.39 |
| 10 | 2.448 | 9.914 | 0.27 | 9.52 |
| | (2.451) | (12.18–13.86) | (0.26) | (4.3–2.3) |
| 11 | 2.381 | 9.663 | 0.25 | 11.14 |
| | (2.378) | (13.29) | (0.14) | (3.6) |

Buffers:

initialized capillary electrophoresis method TRIS/Malic Acid/TRIS 150 mM/L pH 4.605 chondroitin sulphate 1%.

Initiator:

0.25% Pig Albumin in usual capillary electrophoresis method buffer.

usual capillary electrophoresis method TRIS/Malic Acid 150 m/ML pH 4.605.

Marker:

DMF analyzed 9 times for each (ready-to-use) capillary and each method, first by ICEM and then by UCEM for capillaries 1 to 5, first by UCEM then by ICEM for capillaries 6 to 11.

The figures in parentheses were obtained after a prior equilibration of the capillary for 60 min. showing that the capillaries were not stabilized and that in UCEM the migration time is constantly increasing. For this buffer and using a stabilized capillary the EOF time is usually around 14 minutes.

TABLE 6

Direct stabilization of EOF with change of buffers

| Buffer | Time in min. | | RSD | |
|---|---|---|---|---|
| | UCEM | ICEM | UCEM | ICEM |
| Malic/TRIS | 13.29 | 2.378 | 3.6 | 0.14 |
| MALIC/DAP | 27.235 | 3.724 | 0.38 | 0.15 |
| MALIC/ARG | 95.361 | 2.874 | — | 0.14 |
| MALEIC/TRIS | 3.859 | 3.372 | 2.83 | 0.12 |
| MALEIC/ARG | 11.907 | 2.869 | 13 | 0.72 |

Buffers:

initialized capillary electrophoresis method Malic 150 mm/L Maleic 175 mM/L all at pH 4.605—chondroitin sulphate 1%.

Initiator:

0.25 Pig Albumin in usual capillary electrophoresis method buffer usual capillary electrophoresis method 150 mM/L at pH 4.605—no chondroitin sulphate.

Marker:

DMF analyzed 9 times first by UCEM then by ICEM for each buffer.

Capillary:

23,7 cm×25 μ. Same capillary was used and was always equilibrated for each buffer.

DAP: diaminopropane

ARG: arginine

The initialized capillary electrophoresis method stabilizes the EOF particularly at pH around 4–5, where it is usually the most unstable (J. Kohrs and H. Engelhardt, J. Microcol. Sept. 1991; 3:491), meaning an improvement in the reproducibility of the migration times, of EOF, and of each peak of the analytes (table 7). Furthermore, this method brings an improvement in the reproducibility of the area of each peak (table 8), meaning that the user can have more confidence in identifying a peak by calculating its mobility (qualitative result) and in ascertaining its percentage in a given mixture (quantitative result).

TABLE 7

Reproducibility of migration times (RSD)

| Concentration of chondroitin sulphate | 0% | 0.002% | 0.02% | 0.1% | 0.5% | 1% |
|---|---|---|---|---|---|---|
| Peak 1 | 1.25 | 0.35 | 0.13 | 0.06 | 0.2 | 0.49 |
| Peak 2 | 1.98 | 0.47 | 0.14 | 0.18 | 0.4 | 0.46 |
| Peak 3 | 1.64 | 0.47 | 0.09 | 0.1 | 0.49 | 0.58 |
| Peak 4 | 3.13 | 1 | 0.1 | 0.1 | 0.47 | 0.61 |
| Peak 5 | 3.41 | 1.04 | 0.11 | 0.14 | 0.47 | 0.65 |
| Peak 6 | 3.5 | 1.16 | 0.85 | 0.25 | 0.57 | 0.58* |
| Peak 7 (DMF) | 6.42 | 1.48 | 0.12 | 0.05 | 0.25 | 0.58 |

*peak 6 on peak 7

TABLE 8

Reproducibility of percentage of each peak (RSD) at pH 4.6 (example 1)

| Concentration of chondroitin sulphate | 0% X | 0.002% | 0.02% | 0.1% |
|---|---|---|---|---|
| Peak 1 | 11.81 | 4.1 | 5.5 | 0.54 |
| Peak 2 | 8.88 | 1.5 | 1.7 | 0.27 |
| Peak 3 | 17.85 | 3 | 4.28 | 1.4 |
| Peak 4 | 5.54 | 3.36 | 3.6 | 1 |
| Peak 5 | 8.12 | 1.76 | 5.4 | 3.8 |
| Peak 6 | 42.6 | 16.5 | 13.4 | 12.75 |
| Peak 7 (DMF) | 6.29 | 4 | 10.8 | 12.2 |

X: baseline corrected values (background values between 6 and 13%. In the presence of chondroitin sulphate no background correction was made.

The initialized capillary electrophoresis method increases the EOF and thus the velocities of the substances, which is reflected by a shortening of the migration times (table 9). The magnitude of this effect varies with the nature of the buffer, the molarity of the buffer, the ionic strength of the buffer, the pH of the buffer, the percentage of polyanion(s), the percentage of initiator or the rinsing time of initiator, and changes from one polyanion to another (table 2) and from one initiator to another (table 1). The internal diameter of the capillary also affects the increase in EOF. For example, at 5 KV, using a buffer Malic/TRIS 25 mM/l, pH 4.922, with 75 µ ID, $t_{eof}$ is measured at 14.615 min., while in the presence of polybrene 0,001% and chondroitin sulphate 0.01% it becomes 3.942 min. Using the same buffer at 37.5 mM/l pH 4.8 with a 50 µID, $t_{eof}$ is measured at 3.194 min. while in the presence of polybrene 0.001% and chondroitin 0.01% it becomes 2.269 min.

TABLE 9

Shortening of migration time in min. (AVG of 9) Example 1

| Concentration of chondroitin sulphate | UCEM 0% | ICEM 0.002% | ICEM 0.02% | ICEM 0.1% | ICEM 0.5% | ICEM 1% |
|---|---|---|---|---|---|---|
| Peak 1 | 2.769 | 2.573 | 1.692 | 1.645 | 1.617 | 1.748 |
| Peak 2 | 2.952 | 2.757 | 1.766 | 1.716 | 1.69 | 1.821 |
| Peak 3 | 3.74 | 3.364 | 1.974 | 1.909 | 1.868 | 2.023 |
| Peak 4 | 7.291 | 5.93 | 2.629 | 2.51 | 2.419 | 2.648 |
| Peak 5 | 8.042 | 6.416 | 2.724 | 2.596 | 2.498 | 2.743 |
| Peak 6 | 8.859 | 6.912 | 2.783 | 2.631 | 2.539 | 3.181 |
| Peak 7 (DMF) | 17.893 | 10.969 | 3.287 | 3.085 | 2.92 | 3.181 |

Generally, in conditions leading to a weak EOF such as high molarity, low pH, the presence of EOF reducers or inhibitors in the buffer like PEG, PVP and amines, the effect on the increase of EOF of the initialized capillary electrophoresis method is strong. In conditions leading to a strong EOF such as low molarity, high pH, and no EOF reducers, on the other hand, the effect on the increase of EOF of the initialized capillary electrophoresis method is weaker (tables 10–11).

TABLE 10

In conditions of high EOF

| | DMF | Peak 1 2–5 | Peak 2 2–6 | Peak 3 2–3 | Peak 4 3–5 |
|---|---|---|---|---|---|
| UCEM time | 1.753 | 7.477 (−0.437) | 8.039 (−0.446) | 8.434 (−0.452) | 13.965 (−0.499) |
| RSD | 0.4 | 2.3 | 2.6 | 2.6 | 5.3 |
| ICEM time | 1.712 | 6.702 (−0.435) | 7.195 (−0.445) | 8.418 (−0.465) | 11.843 (−0.5) |
| RSD | 0.12 | 1.05 | 1.47 | 0.21 | 2.34 |

With regard to the figures in parentheses, mobilities were calculated as follows:

$$\frac{t_{eoF} - t}{t_{eoF} \cdot t}$$

Buffers:
usual capillary electrophoresis method (UCEM):
  buffer phosphate 0.1 M/L pH 10.
initialized capillary electrophoresis method (ICEM):
  buffer as in usual capillary electrophoresis method with 0.1% dextran sulphate MW 500,000.
initiator: polybrene 0.00005%.
sample: 4 positional isomers of dihydroxybenzoic acids.

TABLE 11

In conditions of high EOF

| Peak | UCEM | ICEM | UCEM | ICEM |
|---|---|---|---|---|
| | Migration times in min. | | RSD | |
| DMF | 1.699 | 1.667 | 0.34 | 0.34 |
| γ | 2.076 | 2.027 | 0.66 | 0.91 |
| β | 2.333 | 2.257 | 0.39 | 0.37 |
| α2 | 2.654 | 2.552 | 0.48 | 0.49 |
| α1 | 2.781 | 2.669 | 0.43 | 0.49 |
| Alb | 3.071 | 2.931 | 1.22 | 0.38 |
| Barbital | 3.777 | 3.556 | 0.76 | 0.78 |

TABLE 11-continued

| | In conditions of high EOF | | | |
|---|---|---|---|---|
| Peak | UCEM | ICEM | UCEM | ICEM |
| | Percentages of each peak | | RSD | |
| γ | 13.88 | 14.19 | 5.07 | 4.5 |
| β | 16.19 | 16.06 | 3 | 3.53 |
| α2 | 19.9 | 19.49 | 3.44 | 3.68 |
| α1 | 14.33 | 15.3 | 5.86 | 4.74 |
| Alb | 35.68 | 34.95 | 3.85 | 2.46 |

Buffer:

usual capillary electrophoresis method (UCEM):
   borate 140 mM/L pH 10.005.

initialized capillary electrophoresis method (ICEM):
   same buffer as in usual capillary electrophoresis method with dextran sulphate MW 500,000 0.01%.

initiator: polyethyleneimine MW 600,000 10–6%.

sample: human serum diluted 1/10 in phosphate saline buffer containing DMF and sodium barbital (neutral and acidic markers).

The initialized capillary electrophoresis method increases the EOF in conditions leading to low EOF in such a way that it allows the use of such conditions as high molarity or low pH or the presence of an EOF reducer or any combination of the above (table 12), or even the use of a buffer base including an amine or a diamine. Nevertheless, this method produces migration times differing slightly in absolute value from those obtained with the same buffer but in conditions where the EOF was higher (table 13). This effect is such that it allows the use of a buffer base in which, for example, NaOH has been replaced by an amine base such as TRIS. Such a substitution presents many benefits, such as no (or less) adsorption of cationic species, the use of higher molarity because such amino-buffers are less conductive (resulting in a decrease in the diffusion coefficient), better definition of the peaks which are narrower, and higher resolution with only a slight increase of analysis time (table 12).

The initialized capillary etectrophoresis method allows the use of a buffer of higher molarity or higher ionic strength which results in sharpening of the peaks or rendering them less diffuse and more symmetrical with only a slight increase in migration times, said increase being less important than the increase in migration times which is obtained with a usual capillary electrophoresis method in the same conditions of higher molarity or higher ionic strength (table 12).

TABLE 12

| | In conditions leading to a decrease of EOF (addition of polyethylene glycol 6000) | | | | | |
|---|---|---|---|---|---|---|
| Concentration of buffer | 125 mM/L | | 250 mM/L | | 500 mM/L | |
| UCEM | | +PEG | | +PEG | | +PEG |
| Time | 1.835 | 3.296 | 2.37 | 4.748 | 3.415 | 6.951 |
| RSD | 0.95 | 0.53 | 1.89 | 1.3 | 2 | 1.72 |
| ICEM | | +PEG | | +PEG | | +PEG |
| 0.04% | | | | | | |
| Time | 2.123 | 2.154 | 2.455 | 2.497 | 3.213 | 3.293 |
| RSD | 0 | 0.2 | 0.98 | 0.17 | 0.36 | 0.57 |

TABLE 12-continued

| | In conditions leading to a decrease of EOF (addition of polyethylene glycol 6000) | | | | | |
|---|---|---|---|---|---|---|
| Concentration of buffer | 125 mM/L | | 250 mM/L | | 500 mM/L | |
| 0.2% | | | | | | |
| Time | 2.054 | 2.076 | 2.366 | 2.404 | 3.001 | 3.099 |
| RSD | 0.034 | 0.18 | 0.34 | 0.42 | 0.41 | 0.29 |
| 1% | | | | | | |
| Time | 2.012 | 2.038 | 2.278 | 2.307 ﹢ | 2.823 | 2.85 |
| RSD | 0 | 0.24 | 0.05 | 0.31 | 0.23 | 0.31 |

Buffer:

usual capillary electrophoresis method (UCEM):
   Acetate/TRIS pH 4.65 at 3 different concentrations (0.04%–0.2%–1%).

initialized capillary electrophoresis method (ICEM):
   as in usual capillary electrophoresis method but with chondroitin sulphate, each concentration with different concentrations of chondroitin sulphate.

initiator:
   pig albumin 0.25% in usual capillary electrophoresis method buffer.

+: buffer with added PEG

TABLE 13

| Comparison between Malic/NaOH and Malic/TRIS buffers | | |
|---|---|---|
| | Malic/NaOH | Malic/TRIS |
| UCEM Avg. time | 10.679 | 16.802 |
| RSD | 3.47 | 1.85 |
| UCEM Avg. time | 2.479 | 2.9 |
| RSD | 0.36 | 0.15 |

Buffer:

usual capillary electrophoresis method (UCEM):
   Malic acid/NaOH or Malic/TRIS both 150 mM/L Malic acid and pH 4.605.

initialized capillary electrophoresis method (ICEM):
   as in usual capillary electrophoresis method but containing 1% chondroitin sulphate.

initiator:
   Pig Albumin 0.25% in usual capillary electrophoresis method buffer.

The initialized capillary electrophoresis method does not modify the mobilities of negatively charged substances (table 20) provided these negatively charged substances do not contain polarizable groups which can interact with either the acidic group of the polyanion or with a polarizable group of the polyanion. An example of such interaction can be found in table 10 for peak 3 (2–3 dihydroxy benzoic acid) which displays a change of mobility in the presence of the polyanion. Then it is possible, using the initialized capillary electrophoresis method, to separate substances having the same negative charge but differing either by a polarizable group or having the same polarizable group but at different positions or having functional or polarizable groups with different interaction or complexation constants. The initialized capillary electrophoresis method decreases the mobility of substances which are positively charged at the running buffer pH (table 14). Furthermore, polarizable groups on neutral or positive substances can also interact with the polyanion and then it is possible to separate by the initialized capillary electrophoresis method neutral substances or positive substances of the same charge when they differ by the position of the polarizable group or when they differ by their interaction or complexation constants. The last column of table 14 demonstrates that this effect increases when the polarizability of the molecule increases ($OCF_3 > Br > Cl > F > OCH_3$).

TABLE 14

Decrease of mobilities of positive substances by polyanions (example 1) and relative decrease of mobilities in function of the polarizable group (in parentheses).
"Mobilities" are calculated based on the average migration time (9 replicates) and expressed as $$\frac{t_{eoF} - t}{t_{eoF} \cdot t}$$

and the relative decrease in mobilities is expressed as $$\frac{v_{0\%} - v}{v} \cdot 100\%$$

| Para substituent | Concentration of chondroitin sulphate | | | | | |
|---|---|---|---|---|---|---|
| | 0% | 0.002% | 0.02% | 0.1% | 0.5% | 1% |
| OCH₃ | 0.305 | 0.297 (3) | 0.287 (6) | 0.284 (7) | 0.276 (10) | 0.256 (16) |
| CH₃ | 0.283 | 0.272 (4) | 0.262 (7) | 0.259 (8) | 0.246 (13) | 0.235 (17) |
| F | 0.211 | 0.207 (2) | 0.202 (4) | 0.2 (5) | 0.193 (9) | 0.18 (15) |
| Cl | 0.081 | 0.077 (5) | 0.076 (6) | 0.074 (9) | 0.071 (12) | 0.063 (22) |
| Br | 0.068 | 0.065 (4) | 0.063 (7) | 0.061 (10) | 0.058 (15) | 0.05 (93) |
| OCF₃ | 0.057 | 0.057 (0) | 0.055 (4) | 0.056 (2) | 0.051 (11) | 0 (100) |

The initialized capillary electrophoresis method increases the number of theoretical plates (N) of neutral and negative substances and usually of positive substances, too, given it decreases the migration times.

Indeed, $$N = \frac{L^2}{2D \cdot t}$$

L: length of the capillary
D: diffusion coefficient
t: migration times

The initialized capillary electrophoresis method unexpectedly increases the efficiency despite the decrease in the migration times.

The efficiency is expressed as:

$$Ef = 16 \left( \frac{t}{w} \right)^2$$

where:
t is the migration time of a component in sec., and
w is the peak width in sec. at the base line.

The increase in efficiency is illustrated by table 15, which shows that the decrease in the migration times resulting from the initialized capillary electrophoresis method is more than compensated for by the reduction in the peak width, resulting in a higher ratio $(t/w)^2$.

TABLE 15

Comparison of efficiency between usual capillary electrophoresis method and initialized capillary electrophoresis method.

| Peak | 1 | 2 | 3 | 4 | 5 | 6 |
|---|---|---|---|---|---|---|
| UCEM | 94376 | 81498 | 36660 | 60254 | 52264 | 72474 |
| ICEM | 95222 | 93154 | 55272 | 85822 | 219396 | 120414 |

Same conditions as in table 16.

The initialized capillary electrophoresis method increases the resolution while increasing the velocities. The initialized capillary electrophoresis method also allows one to analyze a mixture of neutral, negative and positive components in a single run (examples 1 and 2).

Furthermore, the initialized capillary electrophoresis method smoothes the base-line with the result that usually no more base-line adjust or correction is needed before quantification (table 16). This property is also reflected by the improvement of the reproducibility of the peaks areas. It is speculated that the initiator saturates the capillary wall and that the excess of initiator is eliminated during the subsequent rinsing step, preventing any further adsorption and any release during the electrophoresis of adsorbed cationic species coming from a previously analyzed sample or coming from the buffer. Indeed, if the charge of such adsorbed species is such that they can migrate towards the cathode, they may cause either spurious peaks or cause a continuous drift of the base-line. If there is a release of adsorbed initiator, the released initiator migrates towards the cathode and then will never pass the detector.

TABLE 16

Comparison of base-line or background between UCEM and ICEM (5 replicates).

| Peak | Migration Time | RSD | % of each peak | RSD | Background |
|---|---|---|---|---|---|
| Usual capillary electrophoresis method | | | | | |
| 1 | 2.584 | 2.4 | 7.9 | 22.5 | |
| 2 | 3.357 | 2.75 | 10 | 23.3 | |
| 3 | 3.496 | 2.94 | 15.5 | 20.6 | |
| 4 | 3.735 | 3 | 13.65 | 22.1 | |
| 5 | 4.302 | 3.5 | 14.99 | 17.35 | |
| 6 | 7.582 | 5.49 | 14.19 | 19.53 | |
| | | | 72.27 | | 27.73% |
| Initialized capillary electrophoresis method | | | | | |
| 1 | 1.755 | 0.43 | 12.46 | 0.84 | |
| 2 | 1.92 | 0.5 | 12.09 | 3.5 | |
| 3 | 1.96 | 0.53 | 19.8 | 3.55 | |
| 4 | 2.029 | 0.48 | 17.31 | 3 | |
| 5 | 2.175 | 0.62 | 18.642 | 1.3 | |
| 6 | 2.736 | 0.75 | 18.15 | 2.1 | |
| | | | 98.45 | | 1.55% |

Buffer:
UCEM: Malic acid 150 mM/L TRIS pH 4.625.
ICEM: same buffer as UCEM with 0.01% chondroitin sulphate.
initiator: pig albumin 0.2% in usual capillary electrophoresis method buffer.
sample: six positional isomers of dimethylaneline at low concentration to have a low signal/background ratio.
Since the detection occurs on-capillary, slower moving components spend more time migrating past the detector window than do the more rapid components. Consequently, the more slowly moving zones produce an increase in the peak area counts, marked by a broadening at the peak base. When quantifying solutes present in a mixture, a correction factor must be applied to normalize the peak areas as a function of the migration velocity. As can be seen from tables 9 and 17, using the initialized capillary electrophoresis method or normal capillary electrophoresis methods the slowest peaks are the most affected in their migration times, which means that the correction factor may come close to 1 when analyzing samples which do not differ a lot by their migration times, which is not true in usual capillary electrophoresis methods (table 18).

TABLE 17

Data at pH 2.507 Positively charged substances
Example 3

| Peak | CV on migration time (mean of 9) | | Migration times (mean of 9) | | Mobility $\frac{t_{eoF} - t}{t_{eoF} \cdot t}$ | |
|---|---|---|---|---|---|---|
| | UCEM | ICEM | UCEM | ICEM | UCEM | ICEM |
| Nicotinic | 1.04 | 0.52 | 5.577 | 1.497 | 0.112 | 0.075 |
| Isonicotinic | 1.79 | 0.51 | 8.331 | 1.611 | 0.053 | 0.028 |
| Picolinic | 3.43 | 0.011 | 13.669 | 1.699 | 0.0057 | -0.0045 |
| DMF | 3.77 | 0.35 | 14.834 | 1.686 | | |

Table 18 Comparison between percentage of each peak not corrected or corrected in function of migration time (experiment table 17)—Mean of 9–CV in parentheses.

TABLE 18

Comparison between percentage of each peak not corrected or corrected in function of migration time (experiment table 17) - Mean of 9 - CV in parentheses.

| | UCEM | | ICEM | |
|---|---|---|---|---|
| | Not Corrected | Corrected | Not Corrected | Corrected |
| Nicotinic | 18.5 | 30.65 | 31.14 | 33.27 |
| | (10.65) | (7.75) | (0.28) | (0.2) |
| Isonicotinic | 32.38 | 35.9 | 37.22 | 36.94 |
| | (4.19) | (1.72) | (0.14) | (0.11) |
| Picolinic + DMF | 49.21 | 33.44 | 31.64 | 29.78 |
| | (6.62) | (8.3) | (0.38) | (0.25) |

The initialized capillary electrophoresis method minimizes the variation of the electroosmotic flow, as shown in table 19.

The initialized capillary electrophoresis method is highly reproducible. A neutral marker is not needed for the migration times and for the area of each peak, outside of calculating mobilities, which means that when analyzing either neutral and positive or neutral and negative substances or the three together, there is no interference by the marker which can hide a neutral substance at low concentration, for example. This also facilitates quantification, as there is no more need to subtract the percentage of the marker and then normalize the quantitative results.

TABLE 19

Variation and reproducibility of electroosmotic flow as a function of pH

| pH | UCEM Time | RSD % | ICEM Time | RSD % |
|---|---|---|---|---|
| 1.597 | x | NA | 1.921 | 3.5 |
| 2.999 | >60 | NA | 1.928 | 2.93 |
| 4.003 | 15.827 | 21.4 | 1.744 | 2 |
| 5.014 | 2.411 | 11.5 | 1.656 | 2.15 |
| 5.995 | 1.42 | 5.52 | 1.564 | 1.3 |
| 6.998 | 1.236 | 2.4 | 1.459 | 0.66 |
| 7.998 | 1.143 | 1.1 | 1.401 | 0.61 |
| 9.001 | 1.098 | 0.26 | 1.332 | 0.23 |
| 10.003 | 1.09 | 0.66 | 1.31 | 0.29 | x EOF towards the anode

Buffer:
 usual capillary electrophoresis method $H_3PO_4$ 100 mM/L brought to the required pH by addition of NaOH.
 initialized capillary electrophoresis method as in usual capillary electrophoresis method but containing 0.1% chondroitin sulphate.
Initiator:
 Polybrene 0.001% in usual capillary electrophoresis method.

The marker DMF was analyzed 9 times coming from pH 1.597 and going to 10.003 without equilibration times at each change of pH.

In this case above pH 5 the EOF by ICEM is weaker than by UCEM but changing the initiator and the polyanion and working with some buffer the EOF can be increased (table 10). It is worth noting that one can choose conditions in which ICEM gives slightly lower EOF than UCEM while generating better reproducibilities.

The initialized capillary electrophoresis method generates an electroosmotic flow of the same magnitude for different buffers, the same pH and the same ionic strength (tables 6-12-13-19).

Choosing the appropriate initiator and polyanion, each selected at a defined concentration, it is thus possible with the initialized capillary electrophoresis method to develop a few universal buffers at different pH's. The benefit of such formulations is that they would cover the majority of applications and generate the same EOF, give better qualitative and quantitative reproducibilities, increase the efficiency and the resolution while shortening the analysis time, and increase the throughput, resulting in a decrease in analysis costs.

The above-mentioned properties of the initialized capillary electrophoresis method are also applicable to fields related to capillary electrophoresis, such as in the use of gel filled capillaries, where the use of the invention should allow an increase in the electroosmotic flow in agarose gel-filled capillaries or create an electroosmotic flow in polyacrylamide gel-filled capillaries.

All experiments have been done in exactly the same conditions: the same stabilized capillary (from Polymicro Technology), the same buffer, the same voltage, and the same sample. Results between "initialized capillary electrophoresis method" and "usual capillary electrophoresis method" (i.e., a normal capillary electrophoresis method) can thus be compared.

The present invention also applies to chiral separations when the chiral selector used is not a polyanion itself. Indeed, chiral selectors are molecules such as cyclodiotuns, which can include differentially in their cavities components to be analyzed, or such as biliary salts or proteins, which can interact differentially with components to be separated, resulting each time in the formation of bigger molecules which consequently migrate more slowly and then lengthen the migration time. Since the present invention uses a polyanion, which does not interfere with the chiral separator or the species to be separated, chiral separations can be performed in shorter times.

The electrophoretic velocity of a molecule is the result of the vectorial addition of the electroosmotic mobility (or velocity) and the net velocity of the component:

$$V_{el} = V_{eo} + V$$

From this equation it can be seen that neutral substances having a v=0 move with a velocity equal to $v_{eo}$. Increasing $v_{eo}$ by a usual capillary electrophoresis method or normal capillary electrophoresis method increases $v_{el}$, resulting in shorter analysis time.

Negative substances move with a velocity equal to $v_{eo}-v$. In buffer conditions where $v_{eo}-v$ is small, v is very low and the migration time will be very long. In buffer conditions where $v=v_{eo}$ the electroosmotic velocity cannot compensate for the negative velocity of the molecule and $v_{el}$ becomes negative and the molecule will be driven towards the anode and will not pass the detector. Increasing $v_{eo}$ increases $v_{el}$ and reduces the migration time. Furthermore, it is possible to increase $v_{eo}$ in such a way that $v_{eo}$ can compensate the negative velocity of the molecule, $v_{eo}-v$ becoming positive and then negative substances can be detected in conditions where the usual capillary electrophoresis method lets them migrate towards the anode. The mobility of negative substances using ICEM is unchanged.

Positive substances migrate towards the cathode with an initial velocity $v_{el}$ equal to $v_{eo}+v$, v being positive, i.e. their migration directions oppose the migration direction of the polyanions. In this situation a sort of ion-exchange electrokinetic chromatography is realized in which the separation mechanism is based on differential ion-pair formation of positive ions with a polyanion added to the separation solution. Consequently, after some time, depending upon the ratio polyanion/quantity of positive ions, the velocity of the ion-paired ion attains a steady state velocity $v_{el}$ equal to $v_{eo}+v_{ip}$, $v_{ip}$ being the velocity of the ion-paired ion. Then increasing $v_{eo}$ by initialized capillary electrophoresis method increases $v_{el}$ resulting again in shorter migration times. The velocity of positive substances is then increased by usual capillary electrophoresis methods but the mobility of positive substances is decreased due to an ion-pairing mechanism between the positively charged substances and the negatively charged polyanions. It is even possible by increasing the percentage of polyanions or by increasing the ratio of polyanion percentage/quantity of sample to cancel the charge of the positive substance ($v_{ip}=0$) which will then move with a $v_{el}=v_{eo}$, or even to negatively charge the resulting ion-pair, which will then move with $v_{el}=v_{eo}-v_{ip}$.

When conditions are such that $v_{ip}$ becomes greater than $v_{eo}$ the ion-paired analyte will move towards the anode and will not be detected or can be detected using polarity reversal.

It is thus possible by the initialized capillary electrophoresis method to separate positive analytes having identical electrophoretic mobilities if their ion-pair formation constants with a given polyanion are different.

Positive substances bearing polarizable groups can also interact with a polyanion through these polarizable groups (vectorial addition to the ion-pairing velocity).

In capillary electrophoresis, resolution R is given by:

$$R = 0.177 \Delta\mu_{el} \left[ \frac{V}{D(\mu_{eo} = \mu_{el})} \right]^{\frac{1}{2}}$$

where:

V, D are the applied voltage and the diffusion coefficient;

$\Delta \mu_{el}$ is the difference in electrophoretic mobility between two species to be separated;

$\mu_{eo}$ is the electroosmotic mobility; and $\mu_{el}$ is the average electrophoretic mobility of the two species to be separated.

From the equation above it can be seen that if two substances of identical electrophoretic mobility have different ion-pair constants, the substance having the higher ion-pair constant will become less positively charged, meaning that its mobility will decrease more than the one that has a lower ion-pair constant. In this case the difference in electrophoretic mobility $\Delta\mu_{el}$ becomes greater while the average electrophoretic mobility becomes smaller. As a consequence, the third term of the equation increases. Thus, the use of the initialized capillary electrophoresis method can increase the resolution between two species of identical electrophoretic mobility in the absence of polyanion(s) in the buffer.

The above-mentioned properties of the initialized capillary electrophoresis method are also valuable in chiral separation and in micellar electrokinetic chromatography (example 4).

The following examples are provided for the purpose of further illustration only and are not intended to be limitations on the disclosed invention. All experiments have been done on PACE 2000® and/or a Pilot CE® instrument with 6 capillaries (both from Beckman Instruments, CA).

The initialized capillary electrophoresis method increases the number of theoretical plates (N) at least for neutral and negative analytes, given:

$$N = v_{tot} \cdot \frac{L}{2D}$$

where L is the capillary length and D is the diffusion coefficient of the individual solute. As $V_{tot}$ increases, solutes become more mobile and the time during which they can diffuse through the capillary is minimized. It is also probable that the initialized capillary electrophoresis method involving polyanions which are high polymers decreases the diffusion constant, also resulting in an increase of N.

The initialized capillary electrophoresis method decreases the quantity of heat produced by the Joule effect within the capillary, which is proportional to the time during which the voltage is applied, as it affords shorter analysis time. Again, less heat implies a decrease in convection forces.

At the same concentration, the magnitude of the effect of the initialized capillary electrophoresis method varies from one initiator (table 1) to another and from one polyanion to another (table 2). Some polyanions display the effect at a very low concentration. At concentrations above 1%, side-effects such as an increase in viscosity, excessively high current, or a reversal of migration may appear. For both the initiator and the polyanions, the resulting effects vary non-linearly with the concentration going through a maximum. The effects vary with the degree of polymerization (tables 1 and 2). Thus, the usable concentration varies from polyanion to polyanion as a function of a polyanion's viscosity, solubility and gelification properties.

For a given analyte, the ion-pairing constants differ from one polyanion to another, which means that the present concept is highly versatile.

The effect of the polyanions exists whatever the composition of the buffer used but its magnitude for a given polyanion may vary from one buffer to another even when both are at the same pH and/or ionic strength.

TABLE 20

Data on negatively charged substances by ICEM (normal polarity).

| Concentration of chondroitin sulphate | CV on migration times | | | Migration times (min.) | | | Mobility $\frac{t_{eoF} - t}{t_{eoF} \cdot t}$ | | |
|---|---|---|---|---|---|---|---|---|---|
| | 0.02% | 0.1% | 0.5% | 0.02% | 0.1% | 0.5% | 0.02% | 0.1% | 0.5% |
| DMF | $10^{-6}$ | 0.3 | 0.24 | 3.289 | 3.094 | 2.912 | | | |
| Nicotine | 0.09 | 0.04 | 0.12 | 4.917 | 4.459 | 4.075 | −0.1 | −0.099 | −0.098 |
| Isonicotinic | 0.28 | 0.11 | 0.41 | 10.006 | 8.057 | 6.858 | −0.204 | −0.199 | −0.198 |
| Picolinic | 0.17 | 0.4 | 0.35 | 12.273 | 9.41 | 7.828 | −0.223 | −0.217 | −0.216 |

EXAMPLE 1

(Tables 7-8-9-13)
Conditions:
Capillary:
25 μ×23 cm stabilized (same capillary for all experiments).
Buffer:
usual capillary electrophoresis method: 0.142 M/L Malic acid, Arginine pH 4.6.
initialized capillary electrophoresis method: same as in usual capillary electrophoresis method but with chondroitin sulphate at different percentages.
initiator: 0.2% pig albumin in usual capillary electrophoresis method buffer.
Sample:
mixture of para-substituted anilines: methoxy-, methyl-, fluoro-, chromo-, bromo-, and trifluoromethoxy-aniline and dimethylformamide (EOF marker) dissolved in usual capillary electrophoresis method buffer.

| Method: | |
|---|---|
| Usual capillary electrophoresis method | Initialized capillary electrophoresis method |
| 1. Rinse 1 min. buffer usual capillary electrophoresis method<br>2. Inject sample 10 sec.<br>3. Separate 12 KV<br>4. Rinse 0.5 min. NaOH 0.1 M/L | 1. Rinse 0.5 min. initiator<br>2. Rinse 1 min. buffer with chondroitin sulphate<br>3. Inject sample 10 sec.<br>4. Separate 12 KV<br>5. Rinse 0.5 min. NaOH 0.1 M/L |

Sample was analyzed 9 times by usual capillary electrophoresis method, then 9 times by initialized capillary electrophoresis method, each time with an increased amount of polyanion (here chondroitin sulphate).

EXAMPLE 2

(Table 20)
Same conditions as example 1, but sample is an equimolar mixture of nicotinic, isonicotinic and picolinic acids and DMF analyzed 9 times.
To analyze the same sample by usual capillary electrophoresis method requires working with polarity reversal (table 21).

TABLE 21

Data on negatively charged substances by UCEM (example 2) (same conditions as table 20 but with polarity reversal). Equimolar mixture of nicotinic, isonicotinic, picolinic acids (9 replicates).

| | CV on migration time | Migration times (min.) |
|---|---|---|
| Peak 1 | 0.64% | 4.68 |
| Peak 2 | 0.69% | 5.076 |
| Peak 3 | 1.1% | 10.03 |

Mobilities cannot be calculated.

EXAMPLE 3

(table 17)
Conditions:
Capillary:
25 μ×23 cm stabilized in phosphate buffer.
Buffer:
usual capillary electrophoresis method:
phosphate buffer—0.1 M/L pH 2.507—15 KV.
initialized capillary electrophoresis method:
phosphate buffer 0.1 M/L pH 2,507 with 0,1% chondroitin sulphate 15 KV.
initiator: polybrene 0.0005% in phosphate buffer.
sample:
nicotinic, isonicotinic and picolinic acids, DMF in usual capillary electrophoresis method.

EXAMPLE 4

(Table 22)
Conditions:
Capillary:
25 μ×23 cm stabilized in phosphate buffer.
Buffer:
usual capillary electrophoresis method:
phosphate 0.1 M/L 0 025 M/L SDS.
pH 7.027—12 KV.
initialized capillary electrophoresis method:
same buffer as usual capillary electrophoresis method but with two different percentages of chondroitin sulphate.

sample:
chloro-, fluoro-, bromo-, methyl- and methoxy-benzene in triplicate.

TABLE 8

MEKC data.

| Chondroitin sulphate | CV on migration time | | | Migration times - Avg. in min. | | |
|---|---|---|---|---|---|---|
| | UCEM | ICEM | | UCEM | ICEM | |
| | 0% | 0.002% | 0.01% | 0% | 0.002% | 0.01% |
| Peak 1 | 1.78 | 0.94 | 0.4 | 1.933 | 1.917 | 1.831 |
| Peak 2 | 1.29 | 0.69 | 0.64 | 2.44 | 2.419 | 2.33 |
| Peak 3 | 1.53 | 0.54 | 0.74 | 2.63 | 2.59 | 2.51 |
| Peak 4 | 2.64 | 0.2 | 0.95 | 4.458 | 4.354 | 4.10 |
| Peak 5 | 4.68 | 0.78 | 1.9 | 8.132 | 7.879 | 7.076 |

EXAMPLE 5

Conditions:

Separation of glycosylated haemoglobin from Hb and from haemoglobin variant such as HbF, HbS, HbC by ICEM

| Running buffer: | |
|---|---|
| malic acid: | 20.44 g/L |
| arginine: | 40.15 g/L |
| ethylene glycol: | 1 g/L |
| triton: | 0.01 g/L |
| chondroitin sulphate: | 2.05 g/L | pH 4.651

Initiator:

0.5% horse albumin in malic acid/arginine buffer (14 g and 27.5 g/L, respectively).

Sample:

whole blood

Hemolyzing solution:

malic acid 18.2 g/L brought to pH 5.3 with arginine containing 0.1% ethylene glycol, 0.01% triton. X-100, 1% saponin, 1% chondroitin sulphate.

Preparation of the sample to be injected:

200 µl whole blood with 1000 µl of hemolyzing solution and vortexed.

Procedure:

1. Rinse 30 sec. with initiator.
2. Rinse 60 sec. with running buffer.
3. Inject hemolyzed sample 15 seconds.
4. Separate at 08.5 KV for 6 min., detection at 415 nm.
5. Rinse 15 sec. NaOH 0.2 M/L.
6. Rinse 105 sec. with running buffer.

Figure 2:
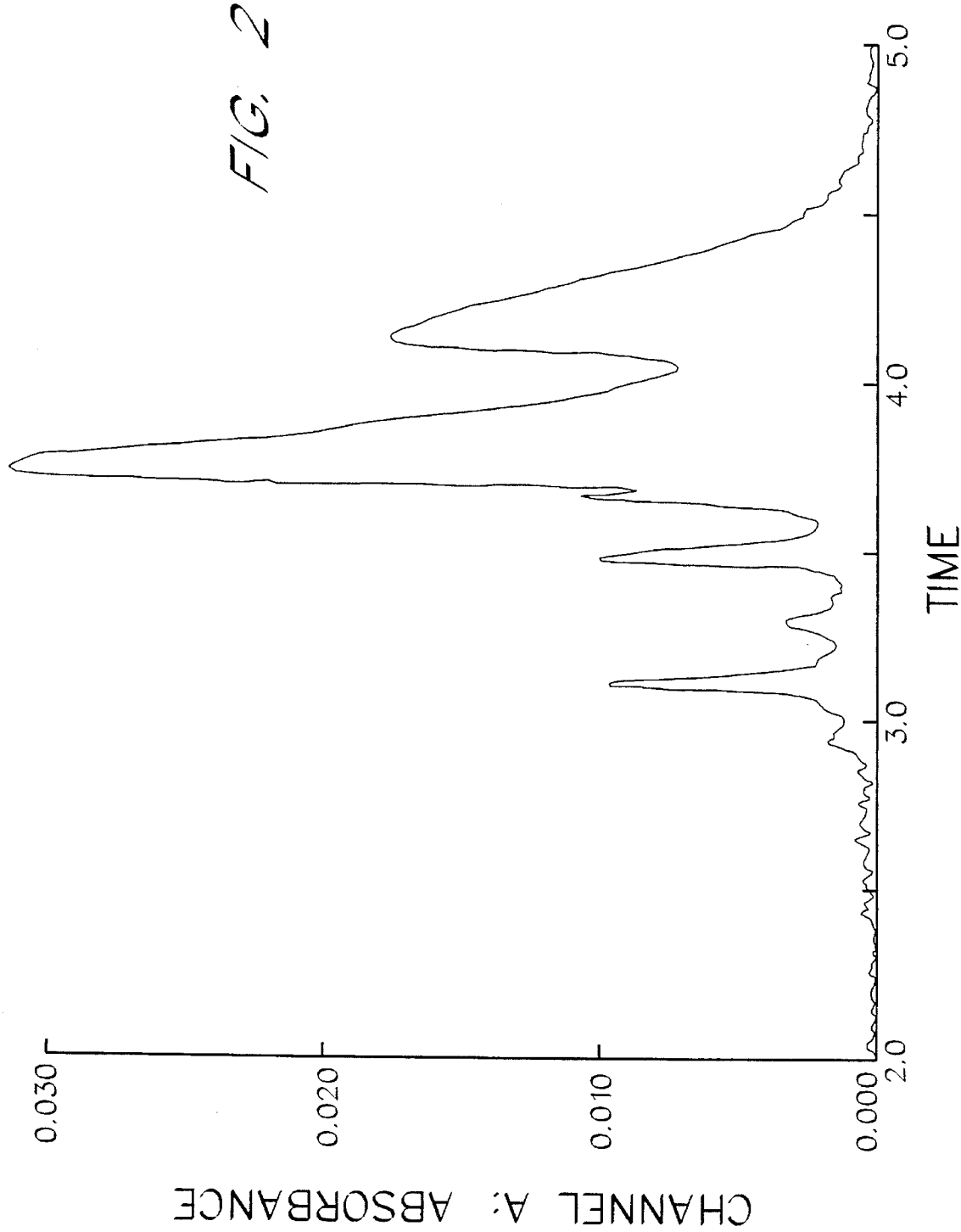
FIG. 2 displays the results of a scan showing the resolution between HbAla, b, HbF, HbAlc, Methemoglobin HbA and Hbs.

FIG. 1 displays a scan showing the resolution between HbAla, HbAlb, HbAlc, methemoglobin and HbA (page 64). FIG. 2 displays a scan showing the resolution between HbAla, b, HbF, HbAlc, methemoglobin, HbA and HbS (page 65).

Although the invention has been described with reference to particular embodiments, those of skill in the art will appreciate that the invention is not limited to these embodiments. In addition, the references cited herein are hereby incorporated by reference.

What we claim is:

1. A capillary electrophoresis method comprising the following steps:

a. rinsing a ready-to-use capillary with an initiator, which produces producing an initialized capillary, said capillary comprising a cathode end and an anode end, said initiator comprising a molecule or a mixture of molecules having a molecular weight higher than 1000 daltons and bearing positive charges at the pH of a capillary buffer used in subsequent step (b), wherein said initiator becomes a polycation when bearing only positive charges and becomes a polyelectrolyte when bearing positive and negative charges;

b. adding a capillary buffer into said initialized capillary, wherein said capillary buffer comprises a polyanion or a mixture of different polyanions, said polyanion or each polyanion in said mixture of polyanions being selected from the group consisting of polysaccharide derivatives, synthetic polymer derivatives, polyacidic amino-acids, polynucleotides, polyphosphoric acids, and a mixture of any of the foregoing, wherein said polyanion or each polyanion in said mixture of polyanions bears a net negative charge at the pH of said capillary buffer;

c. adding a sample to be analyzed into said initialized capillary; and d. submitting said sample to capillary electrophoresis.

2. A method according to claim 1, additionally comprising the step of adding a cathodic buffer to the cathode end of the capillary.

3. A method according to claim 2, wherein said cathodic buffer comprises a polyanion or a mixture of polyanions.

4. A method according to claim 1, additionally comprising the step of adding a sample diluent to said sample.

5. A method according to claim 1, wherein said polyanion or said mixture of polyanions and said initiator are present in said capillary in an amount of between $10^{-12}$ g/100 ml buffer and 5 g/100 ml buffer in said capillary.

6. A method according to claim 1, wherein said initiator is a polymer derivative or a mixture of polymer derivatives having the following structure:

wherein:

$m \times n > 12$;

A is selected from the group consisting of H, OH, NH2, an alkyl group, an aryl group, an alkyl-aryl group, and a heterocyclic group;

B is selected from the group consisting of H, OH, NH2, an alkyl group, an aryl group, an alkyl-aryl group, and a heterocyclic group;

$R^1 \ldots R^m$ represents monomers in a polymer, said polymer being a homopolymer when each of said monomers represented by $R^1 \ldots R^m$ is the same and said polymer being a heteropolymer when at least one of said monomers represented by $R^1 \ldots R^m$ is different from other monomers represented by $R^1 \ldots R^m$, wherein each of said monomers is selected from the group consisting of an alkyl group, an aryl group, an alkyl-aryl group, a nucleotide or nucleic acid group, an amino acid or peptide group, a phosphate group, and a heterocyclic group, and wherein each of said monomers is substituted with a corresponding Y group and with a corresponding W group;

each W group represented by ($W^1 \ldots W^m$) is an atom or chemical group selected from the group consisting of H, imine, primary amine, secondary amine, tertiary amine, quaternary amine, a guanidine group and a hydrazine group; and each Y group represented by ($Y^1 \ldots Y^m$) is an atom or chemical group selected from the group consisting of H and an acidic radical;

said initiator bearing a net positive charge at the pH of said capillary buffer.

7. A method according to claim 6, wherein each of said monomers in said initiator is the same and wherein said monomer contains at least one nitrogen atom.

8. A method according to claim 6, wherein said initiator is a polypeptide or a protein.

9. A method according to claim 6, wherein said polyanion or said mixture of polyanions and said initiator are present in said capillary in an amount of between $10^{-12}$ g/100 ml buffer and 5 g/100 ml buffer in said capillary.

10. A method according to claim 6, wherein said polyanion or each polyanion in said mixture of polyanions has the following structure:

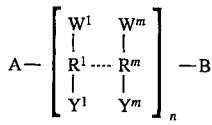

wherein:

mxn>12;

A is selected from the group consisting of H, OH, $NH_2$, an alkyl group, an aryl group, an alkyl-aryl group, and a heterocyclic group;

B is selected from the group consisting of H, OH, $NH_2$, an alkyl group, an aryl group, an alkyl-aryl group, and a heterocyclic group;

$R^1 \ldots R^m$ represents monomers in a polymer, said polymer being a homopolymer when each of said monomers represented by $R^1 \ldots R^m$ is the same and said polymer being a heteropolymer when at least one of said monomers represented by $R^1 \ldots R^m$ is different from other monomers represented by $R^1 \ldots R^m$, wherein each of said monomers is selected from the group consisting of a P (phosphorus) group, an alkyl group, an aryl group, an alkyl-aryl group, and a heterocyclic group, and wherein each of said monomers is substituted with a corresponding Y group and with a corresponding W group;

each W group represented by ($W^1 \ldots W^m$) is an atom or chemical group selected from the group consisting of OH, O, an acidic radical, an alkyl group bearing an acidic radical, an aryl group bearing an acidic radical, an alkyl-aryl group bearing an acidic radical, and a heterocyclic group bearing an acidic radical; and each Y group represented by ($Y^1 \ldots Y^m$) is an atom or chemical group selected from the group consisting of H, OH, an acidic radical, an alkyl group bearing an acidic radical, an aryl group bearing an acidic radical, an alkyl-aryl group bearing an acidic radical, a heterocyclic group bearing an acidic radical, a primary amine, a secondary amine, a tertiary amine, a nitrogenous heterocycle, and a mixture of any of the foregoing;

said polyanion or each polyanion in said mixture of polyanions bearing a net negative charge at the pH of said capillary buffer.

11. A method according to claim 10, wherein said acidic radical is selected from the group consisting of a carboxylic group, a sulphate group, a sulphonate group and a phosphate group.

12. A method according to claim 10, wherein said polyanion or said mixture of polyanions and said initiator are added to said capillary in an amount of between $10^{-12}$ g/100 buffer and 5 g/100 ml buffer in said capillary.

13. A method according to claim 10, wherein said polyanion or each polyanion in said mixture of polyanions is $H_{n+2}P_nO_{3n+1}$ and has the following structure:

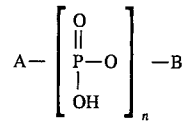

wherein n>12;

A is H or OH; and

B is H or OH.

14. A method according to claim 13, wherein said polyanion or said mixture of polyanions and said initiator are added to said capillary in an amount of between $10^{-12}$ g/100 ml buffer and 5g/100 ml buffer in said capillary.

15. A chemical kit for capillary electrophoresis, comprising an initiator for initializing a capillary, and a capillary buffer to be added into said capillary, said initiator comprising a molecule or a mixture of molecules having a molecular weight higher than 1000 daltons and bearing positive charges at the pH of said capillary buffer, wherein said initiator becomes a polycation when bearing only positive charges and becomes a polyelectrolyte when bearing positive and negative charges, said capillary buffer comprising a polyanion or a mixture of polyanions, said polyanion or each polyanion in said mixture of polyanions being selected from the group consisting of polysaccharide derivatives, synthetic polymer derivatives, polyacidic amino-acids, polynucleotides, polyphosphoric acids, and a mixture of any of the foregoing, wherein said polyanion or each polyanion in said mixture of polyanions bears a net negative charge at the pH of said capillary buffer.

16. A chemical kit according to claim 15, wherein the initiator is a polymer derivative having the following structure:

wherein:

mxn>12;

A is selected from the group consisting of H, OH, NH2, an alkyl group, an aryl group, an alkyl-aryl group, and a heterocyclic group;

is selected from the group consisting of H, OH, NH2, an alkyl group, an aryl group, an alkyl-aryl group, and a heterocyclic group;

$R^1 \ldots R^m$ represents monomers in a polymer, said polymer being a homopolymer when each of said monomers represented by $R^1 \ldots R^m$ is the same and said polymer being a heteropolymer when at least one of said monomers represented by $R \ldots R^m$ is different from other monomers represented by $R^1 \ldots R^m$, wherein each of said monomers is selected from the group consisting of an alkyl group, an aryl group, an alkyl-aryl group, a nucleotide or nucleic acid group, an amino acid or peptide group, a phosphate group, and a heterocyclic group, and wherein each of said monomers is substituted with a corresponding Y group and with a corresponding W group;

each W group ($W^1 \ldots W^m$) is an atom or chemical group selected from the group consisting of H, imine, primary amine, secondary amine, tertiary amine, quaternary amine, a guanidine group and a hydrazine group; and each Y group ($Y^1 \ldots Y^m$) is an atom or chemical group selected from the group consisting of H and an acidic radical;

said initiator bearing a net positive charge at the pH of said capillary buffer.

17. A chemical kit according to claim 16, wherein each of said monomers represented by $R^1 \ldots R^m$ in said initiator is the same and wherein said monomer contains at least one nitrogen atom.

18. A chemical kit according to claim 17, wherein said initiator is a polypeptide or protein.

19. A chemical kit according to claim 15, wherein said polyanion or each polyanion in said mixture of polyanions has the following structure:

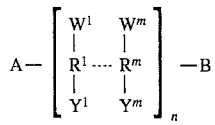

wherein:

m×n>12;

A is selected from the group consisting of H, OH, $NH_2$, an alkyl group, an aryl group, an alkyl-aryl group, and a heterocyclic group;

B is selected from the group consisting of H, OH, $NH_2$, an alkyl group, an aryl group, an alkyl-aryl group, and a heterocyclic group;

$R^1 \ldots R^m$ represents monomers in a polymer, said polymer being a homopolymer when each of said monomers represented by $R^1 \ldots R^m$ are the same and said polymer being a heteropolymer when at least one of the monomers represented by $R \ldots R^m$ is different from other monomers represented by $R^1 \ldots R^m$, wherein each of said monomers is selected from the group consisting of a P (phosphorus) group, an alkyl group, an aryl group, an alkyl-aryl group, and a heterocyclic group, and wherein each of said monomers is substituted with a corresponding Y group and with a corresponding W group;

each W group represented by ($W^1 \ldots W^m$) is an atom or chemical group selected from the group consisting of H, OH, O, an acidic radical, an alkyl group bearing an acidic radical, an aryl group bearing an acidic radical, an alkyl-aryl group bearing an acidic radical, and a heterocyclic group bearing an acidic radical; and each Y group ($Y^1 \ldots Y^m$) is an atom or chemical group selected from the group consisting of H, OH, an acidic radical, an alkyl group bearing an acidic radical, an aryl group bearing an acidic radical, an alkyl-aryl group bearing an acidic radical, a heterocyclic group bearing an acidic radical, a primary amine, a secondary amine, a tertiary amine, a nitrogenous heterocycle, and a mixture of any of the foregoing;

said polyanion or each polyanion in said mixture of polyanions bearing a net negative charge at the pH of said capillary buffer.

20. A chemical kit according to claim 19, wherein the acidic radical is selected from the group consisting of a carboxylic group, a sulphate group, a sulphonate group and a phosphate group.

21. A chemical kit according to claim 20, wherein said polyanion or each polyanion in said mixture of polyanions is $H_{n+2}P_nO_{3n+1}$ and has the following structure:

wherein n>12;

A is H or OH; and

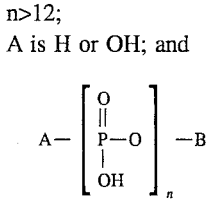

B is H or OH.

22. A chemical kit according to claim 15, further comprising a cathodic buffer comprising a polyanion or a mixture of polyanions.

23. A chemical kit according to claim 22, wherein said polyanion or each polyanion in said mixture of polyanions has the following structure:

wherein:

m×n>12;

A is selected from the group consisting of H, OH, $NH_2$, an alkyl group, an aryl group, an alkyl-aryl group, and a heterocyclic group;

is selected from the group consisting of H, OH, $NH_2$, an alkyl group, an aryl group, an alkyl-aryl group, and a heterocyclic group;

$R^1 \ldots R^m$ represents monomers in a polymer, said polymer being a homopolymer when each of said monomers represented by $R^1 \ldots R^m$ are the same and said polymer being a heteropolymer when at least one of the monomers represented by $R^1 \ldots R^m$ is different from other monomers represented by $R^1 \ldots R^m$ wherein each of said monomers is selected from the group consisting of a P (phosphorus) group, an alkyl group, an aryl group, an alkyl-aryl group, and a heterocyclic group, and wherein each of said monomers is substituted with a corresponding Y group and with a corresponding W group;

each W group represented by ($W^1 \ldots W^m$) is an atom or chemical group selected from the group consisting of H, OH, O, an acidic radical, an alkyl group bearing an acidic radical, an aryl group bearing an acidic radical, an alkyl-aryl group bearing an acidic radical, and a heterocyclic group bearing an acidic radical; and each Y group represented by ($Y^1 \ldots Y^m$) is an atom or chemical group selected from the group consisting of H, OH, an acidic radical, an alkyl group bearing an acidic radical, an aryl group bearing an acidic radical, an alkyl-aryl group bearing an acidic radical, a heterocyclic group bearing an acidic radical, a primary amine, a secondary amine, a tertiary amine, a nitrogenous heterocycle, and a mixture of any of the foregoing;

said polyanion or each polyanion in said mixture of polyanions bearing a net negative charge at the pH of said cathodic buffer.

24. A capillary electrophoresis method comprising the following steps:

a. rinsing a ready-to-use capillary with an initiator, which produces producing an initialized capillary, said capillary comprising a cathode end and an anode end, said initiator comprising a molecule or a mixture of molecules having a molecular weight higher than 1000 daltons and bearing positive charges at the pH of a capillary buffer to be used in subsequent step (b), wherein said initiator becomes a polycation when bearing only a positive charge and becomes a polyelectrolyte when bearing positive and negative charges;

b. adding a capillary buffer into said initialized capillary;

c. injecting a sample to be analyzed into said initialized capillary;

d. adding a cathodic buffer to the cathode end of said capillary, wherein said cathodic buffer comprises a polyanion or a mixture of polyanions, said polyanion or each polyanion in said mixture of polyanions being selected from the group consisting of polysaccharide derivatives, synthetic polymer derivatives, polyacidic amino-acids, polynucleotides, polyphosphoric acids, and a mixture of any of the foregoing, wherein said polyanion or each polyanion in said mixture of polyanions bears a net negative charge at the pH of said cathodic buffer; and e. submitting said sample to capillary electrophoresis.

25. A chemical kit for capillary electrophoresis, comprising an initiator for initiating a capillary comprising a cathode end and an anode end, a capillary buffer to be added into said capillary, and a cathodic buffer to be added to said cathode end of said capillary, said initiator comprising a molecule or a mixture of molecules having a molecular weight higher than 1000 daltons and bearing positive charges at the pH of said capillary buffer, wherein said initiator becomes a polycation when bearing only positive charges and becomes a polyelectrolyte when bearing positive and negative charges, said cathodic buffer comprising a polyanion or a mixture of polyanions, said polyanion or each polyanion in said mixture of polyanions being selected from the group consisting of polysaccharide derivatives, synthetic polymer derivatives, polyacidic amino-acids, polynucleotides, polyphosphoric acids, and a mixture of any of the foregoing, wherein said polyanion or each polyanion in said mixture of polyanions bears a net negative charge at the pH of said cathodic buffer.

* * * * *

UNITED STATES PATENT AND TRADEMARK OFFICE
CERTIFICATE OF CORRECTION

PATENT NO. : 5,611,903  
DATED : March 18, 1997  
INVENTOR(S) : Janssens et al.

Page 1 of 1

It is certified that error appears in the above-identified patent and that said Letters Patent is hereby corrected as shown below:

<u>Column 34, claim 1,</u>  
Line 5, delete the word "producing".

<u>Column 39, claim 24,</u>  
Line 15, delete the word "producing".

Signed and Sealed this

Ninth Day of April, 2002

Attest:

JAMES E. ROGAN  
Attesting Officer  
*Director of the United States Patent and Trademark Office*